US011147722B2

(12) United States Patent
Zhou et al.

(10) Patent No.: US 11,147,722 B2
(45) Date of Patent: Oct. 19, 2021

(54) ABSORBENT ARTICLE WITH A MULTIFUNCTIONAL ACRYLATE SKIN-ADHESIVE COMPOSITION

(75) Inventors: Peiguang Zhou, Appleton, WI (US); Scott W. Wenzel, Neenah, WI (US); Lisha Yu, Appleton, WI (US); Corey Cunningham, Larsen, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1273 days.

(21) Appl. No.: 12/267,806

(22) Filed: Nov. 10, 2008

(65) Prior Publication Data

US 2010/0121304 A1    May 13, 2010

(51) Int. Cl.
| A61F 13/82 | (2006.01) |
| A61F 13/47 | (2006.01) |
| A61F 13/84 | (2006.01) |
| A61L 15/58 | (2006.01) |
| A61F 13/505 | (2006.01) |
| A61F 13/511 | (2006.01) |

(52) U.S. Cl.
CPC .......... *A61F 13/82* (2013.01); *A61F 13/4702* (2013.01); *A61F 13/8405* (2013.01); *A61L 15/58* (2013.01); *A61F 13/505* (2013.01); *A61F 2013/51117* (2013.01)

(58) Field of Classification Search
CPC ............... A61L 15/58; A61L 2300/622; A61L 2300/624; A61F 13/0253; A61F 13/82; A61F 13/47; A61F 13/4702; A61K 9/7038
USPC .... 604/359, 387, 360, 367, 368; 602/48, 52, 602/54–56
See application file for complete search history.

(56) References Cited

U.S. PATENT DOCUMENTS

| 2,693,439 A | 5/1953 | Blanchard et al. |
| 2,842,897 A | 7/1958 | Finn |
| 3,288,346 A | 11/1966 | Peppier |
| 3,338,992 A | 8/1967 | Kinney |
| 3,341,394 A | 9/1967 | Kinney |

(Continued)

FOREIGN PATENT DOCUMENTS

| BR | 9708852 A | 4/1999 |
| BR | 9813625 | 8/2001 |

(Continued)

OTHER PUBLICATIONS

Matsumoto, A. Characteristic polymerization behaviour of microgel-like poly(allyl methacrylate) microspheres. Macromol. Symp. 2002. 179(1), 141-152.*

(Continued)

*Primary Examiner* — Kathryn E Ditmer
(74) *Attorney, Agent, or Firm* — Armstrong Teasdale LLP

(57) ABSTRACT

Improved skin-adhesive compositions for bonding a substrate, such as an absorbent article, to skin are disclosed. More particularly, the skin-adhesive composition has an improved, yet gentle, adhesion to the skin of a user, while maintaining strong, effective bonding to various inanimate, non-skin substrates. In one embodiment, the skin-adhesive composition can provide one or more skin benefit agents to the user. The skin-adhesive composition may applied to an absorbent article, such as a panty-liner, sanitary napkin, or an incontinence article, for directly adhering the article to the skin of a user.

6 Claims, 6 Drawing Sheets

(56) References Cited

U.S. PATENT DOCUMENTS

| | | | |
|---|---|---|---|
| 3,502,538 A | 3/1970 | Petersen | |
| 3,502,763 A | 3/1970 | Hartmann | |
| 3,542,615 A | 11/1970 | Dobo et al. | |
| 3,598,123 A * | 8/1971 | Zaffaroni | 424/435 |
| 3,692,618 A | 9/1972 | Dorschner et al. | |
| 3,731,683 A * | 5/1973 | Zaffaroni | 424/434 |
| 3,797,494 A * | 3/1974 | Zaffaroni | A61F 9/0017 |
| | | | 424/434 |
| 3,802,817 A | 4/1974 | Matsuki et al. | |
| 3,811,438 A | 5/1974 | Economou | |
| 3,849,241 A | 11/1974 | Butin et al. | |
| 3,885,559 A | 5/1975 | Economou | |
| 3,963,029 A | 6/1976 | Brooks | |
| 3,972,328 A * | 8/1976 | Chen | 602/56 |
| 3,973,567 A | 10/1976 | Srinivasan et al. | |
| 3,998,215 A | 12/1976 | Anderson et al. | |
| 4,067,336 A | 1/1978 | Johnson | |
| 4,072,151 A | 2/1978 | Levine | |
| 4,102,945 A * | 7/1978 | Gleave | C09J 4/06 |
| | | | 156/331.1 |
| 4,340,563 A | 7/1982 | Appel et al. | |
| 4,488,928 A | 12/1984 | Ali Khan et al. | |
| 4,505,976 A | 3/1985 | Doehnert et al. | |
| 4,556,056 A | 12/1985 | Fischer et al. | |
| 4,631,062 A | 12/1986 | Lassen et al. | |
| 4,673,403 A | 6/1987 | Lassen et al. | |
| 4,701,509 A * | 10/1987 | Sun | C09J 139/04 |
| | | | 526/264 |
| 4,743,245 A | 5/1988 | Lassen et al. | |
| 4,745,916 A * | 5/1988 | Seber | A61F 13/0253 |
| | | | 128/858 |
| 4,758,241 A | 7/1988 | Papajohn | |
| 4,781,712 A | 11/1988 | Barabino et al. | |
| 4,781,713 A | 11/1988 | Welch et al. | |
| 4,798,603 A | 1/1989 | Meyer et al. | |
| 4,804,380 A | 2/1989 | Lassen et al. | |
| 4,829,099 A * | 5/1989 | Fuller | A61L 24/046 |
| | | | 523/111 |
| 4,846,824 A | 7/1989 | Lassen et al. | |
| 4,879,178 A * | 11/1989 | Sun | A61L 15/585 |
| | | | 428/355 AC |
| 4,909,244 A | 3/1990 | Quarfoot et al. | |
| 4,977,892 A | 12/1990 | Ewall | |
| 5,051,259 A | 9/1991 | Olsen et al. | |
| 5,114,419 A | 5/1992 | Daniel et al. | |
| 5,133,705 A | 7/1992 | Nakanishi et al. | |
| 5,147,938 A | 9/1992 | Kuller | |
| 5,160,328 A | 11/1992 | Cartmell et al. | |
| 5,194,299 A | 3/1993 | Fry | |
| 5,194,550 A | 3/1993 | Rance et al. | |
| 5,221,275 A | 6/1993 | Van Iten | |
| 5,277,954 A | 1/1994 | Carpenter et al. | |
| 5,369,155 A * | 11/1994 | Asmus | 524/55 |
| 5,382,400 A | 1/1995 | Pike et al. | |
| 5,387,208 A | 2/1995 | Ashton et al. | |
| 5,419,956 A * | 5/1995 | Roe | 442/294 |
| 5,445,627 A | 8/1995 | Mizutani et al. | |
| 5,554,381 A | 9/1996 | Roos | A61K 9/7061 |
| | | | 424/448 |
| H1602 H | 10/1996 | Brock | |
| 5,591,146 A * | 1/1997 | Hasse | 604/359 |
| 5,599,335 A | 2/1997 | Goldman et al. | |
| 5,611,790 A | 3/1997 | Osborn, III et al. | |
| 5,614,310 A * | 3/1997 | Delgado et al. | 428/316.6 |
| 5,618,281 A | 4/1997 | Betrabet et al. | |
| 5,618,282 A | 4/1997 | Schlangen | |
| 5,632,736 A | 5/1997 | Block | |
| 5,658,270 A * | 8/1997 | Lichstein | A61F 13/55145 |
| | | | 602/54 |
| 5,662,633 A | 9/1997 | Doak et al. | |
| 5,669,894 A | 9/1997 | Goldman et al. | |
| 5,706,950 A | 1/1998 | Houghton et al. | |
| 5,714,225 A | 2/1998 | Hansen et al. | |
| 5,716,621 A * | 2/1998 | Bello et al. | 424/443 |
| 5,759,560 A | 6/1998 | Dillon | |
| 5,769,837 A | 6/1998 | Parr | |
| 5,800,417 A | 9/1998 | Goerg-Wood et al. | |
| 5,807,367 A | 9/1998 | Dilnik et al. | |
| 5,811,116 A | 9/1998 | Gilman et al. | |
| 5,830,202 A | 11/1998 | Bogdanski et al. | |
| 5,876,855 A * | 3/1999 | Wong | A61L 15/585 |
| | | | 428/355 BL |
| 5,885,265 A | 3/1999 | Osborn, III et al. | |
| 5,897,546 A | 4/1999 | Kido et al. | |
| 5,902,443 A * | 5/1999 | Kanakubo | B41N 1/241 |
| | | | 156/241 |
| 5,910,125 A | 6/1999 | Cummings et al. | |
| 5,994,613 A | 11/1999 | Cummings et al. | |
| 6,045,900 A | 4/2000 | Haffner et al. | |
| 6,080,139 A | 6/2000 | Gallegos | |
| 6,155,265 A | 12/2000 | Hammerslag | |
| 6,156,818 A | 12/2000 | Corzani et al. | |
| 6,177,482 B1 | 1/2001 | Cinelli et al. | |
| 6,187,989 B1 | 2/2001 | Corzani et al. | |
| 6,191,189 B1 | 2/2001 | Cinelli et al. | |
| 6,211,263 B1 | 4/2001 | Cinelli et al. | |
| 6,213,993 B1 | 4/2001 | Zacharias et al. | |
| 6,255,552 B1 | 7/2001 | Cummings et al. | |
| 6,316,524 B1 | 11/2001 | Corzani et al. | |
| 6,336,935 B1 | 1/2002 | Davis et al. | |
| 6,352,528 B1 | 3/2002 | Weber et al. | |
| 6,362,389 B1 | 3/2002 | McDowall et al. | |
| 6,365,645 B1 | 4/2002 | Cinelli et al. | |
| 6,369,126 B1 | 4/2002 | Cinelli et al. | |
| 6,383,630 B1 | 5/2002 | Jauchen et al. | |
| 6,386,203 B1 * | 5/2002 | Hammerslag | 128/898 |
| 6,420,467 B1 * | 7/2002 | Ohtsuka | C08F 290/04 |
| | | | 428/463 |
| 6,479,724 B1 | 11/2002 | Areskoug et al. | |
| 6,491,953 B1 * | 12/2002 | Sojka et al. | 424/490 |
| 6,495,229 B1 | 12/2002 | Carte et al. | |
| 6,565,961 B2 | 5/2003 | Koslow | |
| 6,566,575 B1 * | 5/2003 | Stickels et al. | 602/41 |
| 6,582,411 B1 | 6/2003 | Carstens et al. | |
| 6,613,030 B1 | 9/2003 | Coles et al. | |
| 6,613,955 B1 | 9/2003 | Lindsay et al. | |
| 6,616,643 B1 | 9/2003 | Costa | |
| 6,617,490 B1 | 9/2003 | Chen et al. | |
| 6,620,143 B1 | 9/2003 | Zacharias et al. | |
| 6,632,210 B1 | 10/2003 | Glasgow et al. | |
| 6,641,569 B1 | 11/2003 | Coles et al. | |
| 6,657,009 B2 * | 12/2003 | Zhou | 525/191 |
| 6,659,990 B1 | 12/2003 | Odorzynski et al. | |
| 6,670,402 B1 | 12/2003 | Lee et al. | |
| 6,680,113 B1 * | 1/2004 | Lucast | A61F 13/023 |
| | | | 428/343 |
| 6,683,143 B1 | 1/2004 | Mumich et al. | |
| 6,702,796 B2 | 3/2004 | McFall et al. | |
| 6,733,483 B2 | 5/2004 | Raufman et al. | |
| 6,756,520 B1 * | 6/2004 | Krzysik et al. | 604/360 |
| 6,803,420 B2 | 10/2004 | Cleary et al. | |
| 6,973,931 B1 * | 12/2005 | King | A41G 5/0086 |
| | | | 132/201 |
| 6,997,915 B2 | 2/2006 | Gell et al. | |
| 7,033,342 B2 | 4/2006 | Mizutani et al. | |
| 7,045,559 B2 | 5/2006 | Yahiaoui et al. | |
| 7,053,131 B2 | 5/2006 | Ko et al. | |
| 7,063,859 B1 * | 6/2006 | Kanios et al. | 424/448 |
| 7,122,022 B2 | 10/2006 | Drevik | |
| 7,125,401 B2 | 10/2006 | Yoshimasa | |
| 7,137,971 B2 | 11/2006 | Tanzer | |
| 7,198,689 B2 | 4/2007 | Van Gompel et al. | |
| 7,217,259 B2 | 5/2007 | McDaniel | |
| 7,265,158 B2 | 9/2007 | Risen, Jr. et al. | |
| 7,358,282 B2 | 4/2008 | Krueger et al. | |
| 7,378,450 B2 | 5/2008 | Erkey et al. | |
| 7,468,205 B2 | 12/2008 | Schwerteger et al. | |
| 7,918,837 B2 | 4/2011 | Rosenfeld | |
| 2001/0025163 A1 | 9/2001 | Brown et al. | |
| 2001/0039407 A1 | 11/2001 | Widlund | |
| 2002/0002223 A1 * | 1/2002 | Cox | A61F 13/02 |
| | | | 524/170 |
| 2002/0013565 A1 | 1/2002 | Cinelli et al. | |

(56) References Cited

U.S. PATENT DOCUMENTS

| | | | |
|---|---|---|---|
| 2002/0013566 A1 | 1/2002 | Chappell et al. | |
| 2002/0037977 A1* | 3/2002 | Feldstein et al. | 526/60 |
| 2002/0072725 A1 | 6/2002 | Kolby-Falk et al. | |
| 2002/0156448 A1 | 10/2002 | Steger et al. | |
| 2002/0193766 A1 | 12/2002 | Gell et al. | |
| 2003/0004484 A1 | 1/2003 | Hammons et al. | |
| 2003/0044380 A1* | 3/2003 | Zhu et al. | 424/78.37 |
| 2003/0065302 A1 | 4/2003 | Kuroda et al. | |
| 2003/0065304 A1 | 4/2003 | Bernhard et al. | |
| 2003/0078554 A1 | 4/2003 | Drevik | |
| 2003/0106825 A1 | 6/2003 | Molina et al. | |
| 2003/0170308 A1 | 9/2003 | Cleary et al. | |
| 2003/0203011 A1 | 10/2003 | Abuelyaman et al. | |
| 2003/0208112 A1 | 11/2003 | Schmidt et al. | |
| 2003/0212416 A1* | 11/2003 | Cinelli et al. | 606/134 |
| 2004/0005830 A1* | 1/2004 | Anderson et al. | 442/59 |
| 2004/0019335 A1 | 1/2004 | Moder et al. | |
| 2004/0054342 A1 | 3/2004 | Newbill et al. | |
| 2004/0059310 A1 | 3/2004 | Gagliardi et al. | |
| 2004/0096489 A1* | 5/2004 | Fabo | A61L 15/42 424/449 |
| 2004/0115251 A1* | 6/2004 | Goldman et al. | 424/443 |
| 2004/0116883 A1 | 6/2004 | Krautkramer et al. | |
| 2004/0122385 A1* | 6/2004 | Morman et al. | 604/359 |
| 2004/0133143 A1* | 7/2004 | Burton et al. | 602/58 |
| 2004/0151930 A1 | 8/2004 | Rouns et al. | |
| 2004/0158221 A1 | 8/2004 | Mizutani et al. | |
| 2004/0162539 A1 | 8/2004 | Mizutani et al. | |
| 2004/0167488 A1 | 8/2004 | Bellucci et al. | |
| 2004/0167491 A1 | 8/2004 | Mizutani | |
| 2004/0209075 A1 | 10/2004 | Maloney | |
| 2004/0238393 A1 | 12/2004 | Ohi et al. | |
| 2004/0260263 A1 | 12/2004 | Tamagawa et al. | |
| 2005/0010185 A1* | 1/2005 | Mizutani | A61F 13/47227 604/385.03 |
| 2005/0014901 A1* | 1/2005 | Osae et al. | 525/191 |
| 2005/0036957 A1* | 2/2005 | Prencipe et al. | 424/53 |
| 2005/0059918 A1 | 3/2005 | Sigurjonsson et al. | |
| 2005/0124948 A1 | 6/2005 | Morman et al. | |
| 2005/0124960 A1 | 6/2005 | Ruman | |
| 2005/0136023 A1 | 6/2005 | Yahiaoui et al. | |
| 2005/0136077 A1 | 6/2005 | Yahiaoui et al. | |
| 2005/0137549 A1 | 6/2005 | Lindsay et al. | |
| 2005/0137554 A1 | 6/2005 | Mizutani et al. | |
| 2005/0137561 A1 | 6/2005 | Mizutani et al. | |
| 2005/0148984 A1 | 7/2005 | Lindsay et al. | |
| 2005/0182378 A1 | 8/2005 | Bonelli et al. | |
| 2005/0226917 A1 | 10/2005 | Burton | |
| 2005/0233149 A1* | 10/2005 | Ansell | 428/420 |
| 2005/0244442 A1* | 11/2005 | Sabino et al. | 424/401 |
| 2005/0261652 A1 | 11/2005 | Digiacomantonio et al. | |
| 2006/0058760 A1* | 3/2006 | Rosenfeld et al. | 604/380 |
| 2006/0058764 A1 | 3/2006 | Bohlen et al. | |
| 2006/0063322 A1 | 3/2006 | Hsu et al. | |
| 2006/0079823 A1 | 4/2006 | Utterberg et al. | |
| 2006/0089613 A1* | 4/2006 | Mizutani | A61F 13/47209 604/385.17 |
| 2006/0129114 A1 | 6/2006 | Mason, Jr. et al. | |
| 2006/0142722 A1 | 6/2006 | Koenig et al. | |
| 2006/0148352 A1 | 7/2006 | Munro et al. | |
| 2006/0148917 A1 | 7/2006 | Radwanski et al. | |
| 2006/0161125 A1 | 7/2006 | Bohlen et al. | |
| 2006/0188940 A1* | 8/2006 | Cima et al. | 435/7.1 |
| 2006/0195053 A1 | 8/2006 | Oelund et al. | |
| 2006/0205835 A1* | 9/2006 | Husemann | C08F 20/12 522/71 |
| 2006/0206077 A1 | 9/2006 | Warren et al. | |
| 2006/0210602 A1* | 9/2006 | Sehl | A61L 17/145 424/423 |
| 2006/0216523 A1* | 9/2006 | Takaki | 428/423.1 |
| 2006/0224133 A1 | 10/2006 | Gannon et al. | |
| 2006/0224134 A1 | 10/2006 | Luizzi et al. | |
| 2006/0240087 A1* | 10/2006 | Houze | A61K 8/0208 424/449 |
| 2006/0258788 A1* | 11/2006 | Coggins et al. | 524/386 |
| 2006/0264884 A1 | 11/2006 | Carstens | |
| 2007/0031463 A1* | 2/2007 | Fotinos et al. | 424/405 |
| 2007/0060855 A1* | 3/2007 | Leung | A61L 24/043 602/41 |
| 2007/0100313 A1 | 5/2007 | Luizzi | |
| 2007/0124850 A1 | 6/2007 | Buettner | |
| 2007/0161927 A1 | 7/2007 | Daugirdas | |
| 2007/0179467 A1 | 8/2007 | Shimizu et al. | |
| 2007/0212314 A1* | 9/2007 | Murphy | A61F 13/02 424/66 |
| 2007/0250028 A1 | 10/2007 | Woltman et al. | |
| 2007/0264497 A1* | 11/2007 | Kong | A61L 15/585 428/355 AC |
| 2007/0275068 A1* | 11/2007 | Martens | A61K 9/1611 424/484 |
| 2007/0287973 A1 | 12/2007 | Cohen et al. | |
| 2008/0015535 A1 | 1/2008 | Gannon et al. | |
| 2008/0021424 A1 | 1/2008 | Erdman | |
| 2008/0057811 A1 | 3/2008 | Yahiaoui et al. | |
| 2008/0071237 A1 | 3/2008 | Chen et al. | |
| 2008/0147035 A1 | 6/2008 | Snell | |
| 2008/0154168 A1* | 6/2008 | Luth | A61F 13/0226 602/54 |
| 2008/0161492 A1* | 7/2008 | Cleary et al. | 525/50 |
| 2008/0171958 A1* | 7/2008 | Gundersen | A61F 13/022 602/56 |
| 2008/0175877 A1* | 7/2008 | Ward | A61K 8/0208 424/401 |
| 2008/0207779 A1 | 8/2008 | Yahiaoui et al. | |
| 2008/0234647 A1 | 9/2008 | Arterburn | |
| 2009/0036858 A1 | 2/2009 | Van Den Bogart et al. | |
| 2009/0054864 A1 | 2/2009 | Lira et al. | |
| 2009/0062702 A1* | 3/2009 | Sojka | A41D 13/0531 602/2 |
| 2009/0062761 A1* | 3/2009 | Goerg-Wood et al. | 604/385.01 |
| 2009/0062762 A1 | 3/2009 | Van Himbergen et al. | |
| 2009/0069771 A1 | 3/2009 | Yu et al. | |
| 2009/0069780 A1 | 3/2009 | Plentovich et al. | |
| 2009/0071862 A2 | 3/2009 | Snell | |
| 2009/0118691 A1 | 5/2009 | Rosenfeld | |
| 2009/0171309 A1 | 7/2009 | VanDenBogart et al. | |
| 2009/0182296 A1 | 7/2009 | Dennis et al. | |
| 2009/0198203 A1 | 8/2009 | Lira et al. | |
| 2009/0204090 A1 | 8/2009 | Dennis et al. | |
| 2009/0204092 A1 | 8/2009 | Loyd et al. | |
| 2009/0226498 A1* | 9/2009 | Flugge-Berendes | A61K 31/045 424/411 |
| 2010/0057034 A1 | 3/2010 | Dennis et al. | |
| 2010/0121304 A1 | 5/2010 | Zhou et al. | |
| 2010/0152693 A1 | 6/2010 | Lira et al. | |
| 2010/0198177 A1 | 8/2010 | Yahiaoui et al. | |
| 2011/0092945 A1 | 4/2011 | Carstens | |
| 2011/0135726 A1 | 6/2011 | Munro et al. | |
| 2012/0089107 A1 | 4/2012 | Vandenbogart et al. | |

FOREIGN PATENT DOCUMENTS

| | | |
|---|---|---|
| BR | PI0503829 | 4/2006 |
| DE | 69232589 T2 | 12/2002 |
| EP | 0353972 | 2/1990 |
| EP | 0400895 A1 | 12/1990 |
| EP | 0607986 A1 | 7/1994 |
| EP | 0638303 | 11/1997 |
| EP | 0850628 | 7/1998 |
| EP | 909662 A2 | 4/1999 |
| EP | 0609236 B1 | 5/2002 |
| EP | 1407737 A1 | 4/2004 |
| EP | 1426025 A1 | 6/2004 |
| EP | 1468661 | 10/2004 |
| EP | 1649873 A2 | 4/2006 |
| EP | 1407743 B1 | 1/2010 |
| GB | 2284767 | 6/1995 |
| GB | 2430686 A | 4/2007 |
| JP | 04279159 | 10/1992 |
| JP | 9117473 A | 5/1997 |
| JP | 2004129923 A | 4/2004 |

(56) References Cited

FOREIGN PATENT DOCUMENTS

| KR | 1020010022000 A | 3/2001 |
|---|---|---|
| KR | 100563880 B1 | 3/2006 |
| RU | 2276998 | 5/2006 |
| RU | 2277891 | 6/2006 |
| RU | 2286801 C2 | 11/2006 |
| WO | 1993007841 A1 | 4/1993 |
| WO | 95016424 | 6/1995 |
| WO | 98027910 | 7/1998 |
| WO | 98027912 | 7/1998 |
| WO | 98027913 | 7/1998 |
| WO | 98027915 | 7/1998 |
| WO | 98027916 | 7/1998 |
| WO | 98027917 | 7/1998 |
| WO | 98027918 | 7/1998 |
| WO | 98028015 | 7/1998 |
| WO | 98028017 | 7/1998 |
| WO | 98028019 | 7/1998 |
| WO | 98028022 | 7/1998 |
| WO | 98028023 | 7/1998 |
| WO | 9847454 | 10/1998 |
| WO | 9857609 A1 | 12/1998 |
| WO | 98055065 | 12/1998 |
| WO | 99001094 | 1/1999 |
| WO | 99001095 | 1/1999 |
| WO | 9930659 A1 | 6/1999 |
| WO | 2000000235 | 1/2000 |
| WO | 2000068542 A1 | 11/2000 |
| WO | 2001026595 A1 | 4/2001 |
| WO | 2001060300 A1 | 8/2001 |
| WO | 2002087642 A2 | 5/2002 |
| WO | 2002087645 A1 | 11/2002 |
| WO | 2002094160 A1 | 11/2002 |
| WO | 03/062343 A1 | 7/2003 |
| WO | 2003062343 A1 | 7/2003 |
| WO | 2003103420 A1 | 12/2003 |
| WO | 200493766 A1 | 11/2004 |
| WO | 2006028612 A1 | 3/2006 |
| WO | 2010077306 A1 | 7/2010 |

OTHER PUBLICATIONS

Spindler, R et al. Poly-Pore, a microparticle delivery system: this material offers sustained release, protects sensitive materials and provides multifunctional benefits in personal care formulations. Household & Personal Products Industry. May 1, 2002.*
Final Rule for U.S. Antiperspirant Drug Products for Over-the-Counter Human Use; Final Monograph, vol. 68, No. 110 Fed. Reg. 34273-34293 (Jun. 9, 2003).
21 C.F.R. 350.3 (2008).
21 C.F.R. 350.10 (2008).
Jillian Lloyd, Naomi Crouch, Catherine Minto, Lih-Mei Liao, Sarah Creighton, Female Genital Appearance: 'Normality' Unfolds, BJOG: An International Journal of Obstetrics and Gynecology, May 2005, vol. 112, pp. 643-646, Blackwell Publishing.
Berner et al., Photo Initiators—An Overview, J. Radiation Curing (Apr. 1979), pp. 29.
Mahdavi et al., A Biodegradable and Biocompatible Gecko-inspired Tissue Adhesive, PNAS, vol. 105: 7, pp. 2307-2312.
International Search Report and Written Opinion of PCT/IB2009/054647 dated May 31, 2010.
American Society for Testing Materials (ASTM) Designation: D1300-53 T, "Tentative Specifications and Methods of Test for Laminated Thermosetting Decorative Sheets," pp. 148-166, issued 1953.
Non-final Office Action received in U.S. Appl. No. 12/364,421 dated Sep. 6, 2011.
Australian Patent Examination Report for Patent Application No. 2008285169, dated Nov. 22, 2012; 4 pages.
Translation of Russian Patent Examination Report for Patent Application No. 2011123315, dated Feb. 25, 2013; 3 pages.
Chinese First Office Action for Patent Application No. 201080006001.7, dated Jan. 31, 2013; 12 pages.
Supplemental European Search Report from EP Application No. 08789525.6 dated Sep. 21, 2012.
International Search Report for PCT/IB2009/05073 dated Mar. 26, 2010; 13 pages.
International Search Report for PCT/IB2009/05074 dated Mar. 26, 2010; 11 pages.
International Search Report for PCT/IB2010/050407 dated Oct. 21, 2010; 10 pages.
International Search Report for PCT/IB2010/050408 dated Nov. 1, 2010; 10 pages.
Supplemental European Search Report for Patent Application No. 09824477.5-1303, dated Jun. 7, 2013, 4 pages.
Second Office Action from CN Application No. 200980138546.0, dated Sep. 13, 2013, 11 pages.
International Search Report for PCT/IB2010/050416 dated Nov. 1, 2010; 8 pages.
Product specification of Reemay® Spunbonded Polyester Nonwovens, Style# 2214, found at http://filters.kavonfilter.com/item/filter-paper/reemay-spunbonded-polyester-nonwovens/item-1117? (1 page).
Second Examination Result received in Columbian Patent Application No. 11-95035, dated Oct. 18, 2013.
First Office Action from Russian Patent Application No. 2011136300, dated Jan. 31, 2014; 3 pages.
Office action issued in Korean Patent Application No. 10-2011-7018003 (dated May 2016).
Extended European Search Report received in EP Patent Application 10735556.2, dated Mar. 6, 2014, 8 pages.
International Search Report and Written Opinion for PCT/IB2009/055744 dated Sep. 14, 2010, 8 pages.
BR Technical Report for related application PI0911690-7, dated May 2, 2019, 5 pages.

* cited by examiner

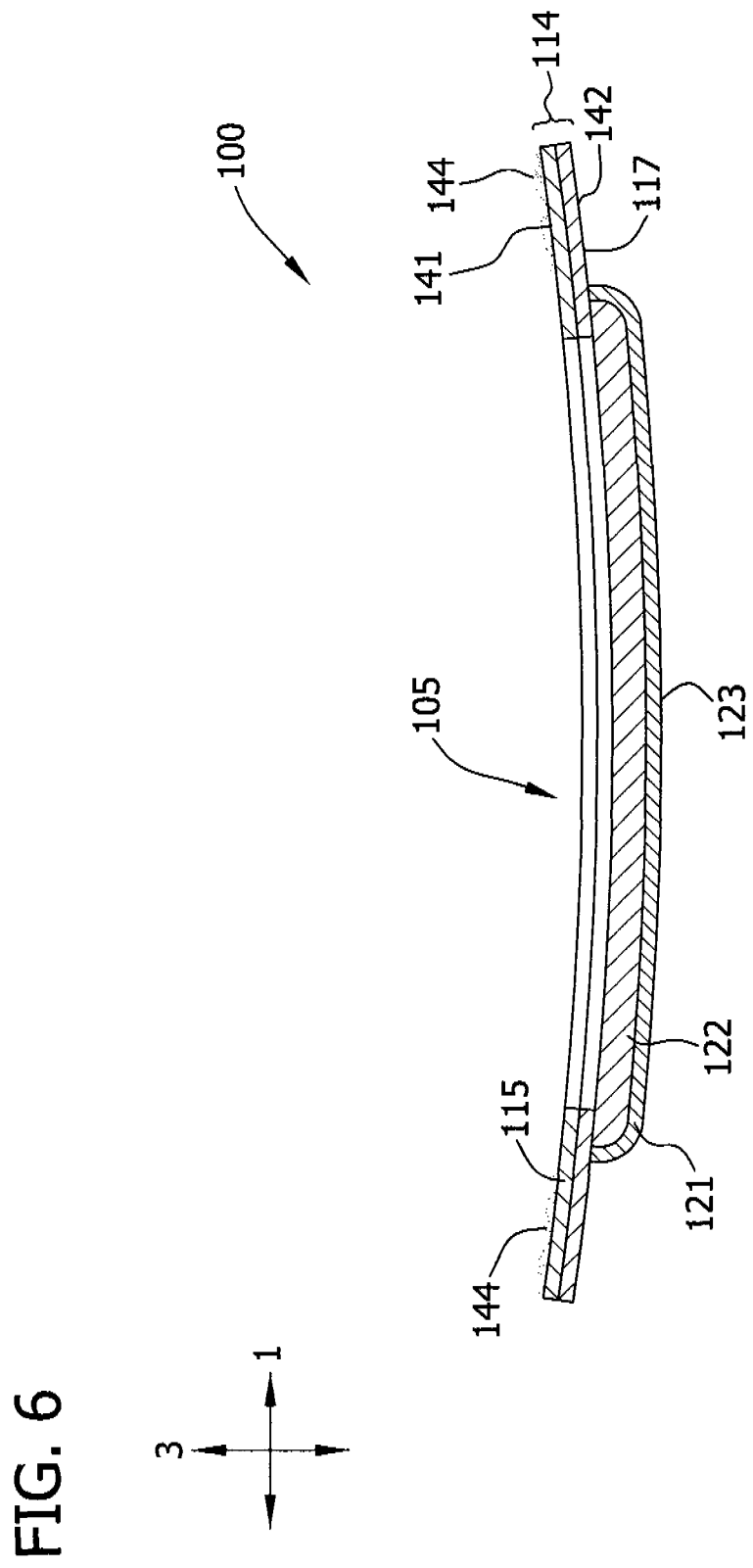

ABSORBENT ARTICLE WITH A MULTIFUNCTIONAL ACRYLATE SKIN-ADHESIVE COMPOSITION

BACKGROUND OF THE DISCLOSURE

The present disclosure relates generally to improved skin-adhesive compositions for bonding a substrate, such as an absorbent article, to skin. More particularly, the skin-adhesive composition has an improved, yet gentle, adhesion to the skin of a user. Furthermore, it has been found that the skin-adhesive composition can maintain, or even have an improved bonding effect to the non-skin substrate. In one embodiment, the present disclosure relates to an absorbent article, such as a panty-liner, sanitary napkin, or an incontinence article, having the skin-adhesive composition applied thereon for directly adhering the article to the skin of a user/wearer.

Absorbent personal care articles intended to absorb discharged bodily fluids are well known in the art. Such absorbent articles generally comprise a fibrous mass or other absorbent core which can absorb and hold body fluids. Similarly, it is well known that feminine care articles have been employed to absorb and hold liquids, such as urine and/or menses. A typical structure of an absorbent article includes a fluid impermeable back sheet, a fluid permeable top sheet and an absorbent core positioned between the back sheet and the top sheet. Prior absorbent articles have also included various other features to improve fluid handling, such as intake layers, distribution layers, retention layers and the like. In these absorbent personal care articles, the top sheet is the body-facing side of the absorbent article and the back sheet is the garment-facing side of the absorbent article.

Generally, the absorbent articles are held in place during use by using the wearer's waist and elastic materials in the waist portion of the absorbent product in place during use, in the case of pant-like garments, such as diapers and training pants, or by attaching the absorbent article to the underwear or undergarment of a wearer, in the case of pads or panty-liners. Current methods of attaching the absorbent article to the underwear or undergarment of a wearer include placing an adhesive on the garment-facing side of the back sheet, having optional flaps (wings) that extend from the longitudinal sides of the absorbent article which wrap around the crotch portion of the underwear or undergarment of the wearer and a combination of the adhesive and the flaps.

It has also been suggested to use an adhesive to adhere the absorbent article to the skin of the wearer. However, currently commercially used skin-adhesive compositions are still in the development stages. Particularly, there is a large gap in terms of adhesion requirements between medical adhesive use and everyday adhesive use. For example, the bonding strength for personal care applications is much lower, and may need to be re-attachable, as compared to that for medical applications. Furthermore, a higher water-vapor transfer rate (WVTR) or anti-sweating standard is needed since personal care products are being used in the areas of the body where most users perspire the heaviest and become the most sweaty, such as pants, diapers, and the like, particularly for more active users.

As such, there is a significant need for skin-adhesive compositions that provide gentle but sufficient attachment to the skin's surface. Particularly, the skin-adhesive composition should allow an improved seal between a substrate and the user's skin to prevent leakage of bodily fluids, while further being gentle to remove. It would be further advantageous if the skin-adhesive composition could deliver multiple skin care benefits, such as antiperspirants and skin moisturizers, to the user during use.

BRIEF DESCRIPTION OF THE DISCLOSURE

It has been found that skin-adhesive compositions can be produced and applied to substrates and articles for improved bonding of the substrates and articles directly to the skin surface of a user. Particularly, the skin-adhesive compositions provide improved, yet gentle, bonding to the skin's surface. Generally, the skin-adhesive composition of the present disclosure includes an acrylate-based adhesive and an adhesion modifier. It has been found that the adhesion modifier can allow the adhesive to maintain its bonding strength with the substrate and have improved bonding strength with the skin, yet remain gentle on the skin's surface. In one embodiment, the skin-adhesive composition can further include at least one skin benefit agent for providing improved skin health to the user.

The skin-adhesive composition can be applied to various substrates. Particularly, in one embodiment, the skin-adhesive composition is applied to the body-facing side of an absorbent article such as a panty-liner, sanitary napkin, or incontinent article.

Accordingly, the present disclosure is directed to a skin-adhesive composition for bonding a substrate to the skin. The adhesive composition comprises an acrylate-based adhesive and an adhesion modifier.

In another aspect, the present disclosure is directed to an absorbent article comprising an absorbent structure and a shell, the shell having a body-facing surface and a garment-facing surface, the body-facing surface having a skin-adhesive composition thereon for adhering the shell directly to a wearer. The skin-adhesive composition comprises an acrylate-based adhesive and an adhesion modifier.

Other objects and features will be in part apparent and in part pointed out hereinafter.

BRIEF DESCRIPTION OF THE DRAWINGS

FIG. 6 shows a side cut-away view of an embodiment of an absorbent article of the present disclosure shown in FIG. 2 along line 5-5 having a two-layer shell.

DEFINITIONS

Figure 1:
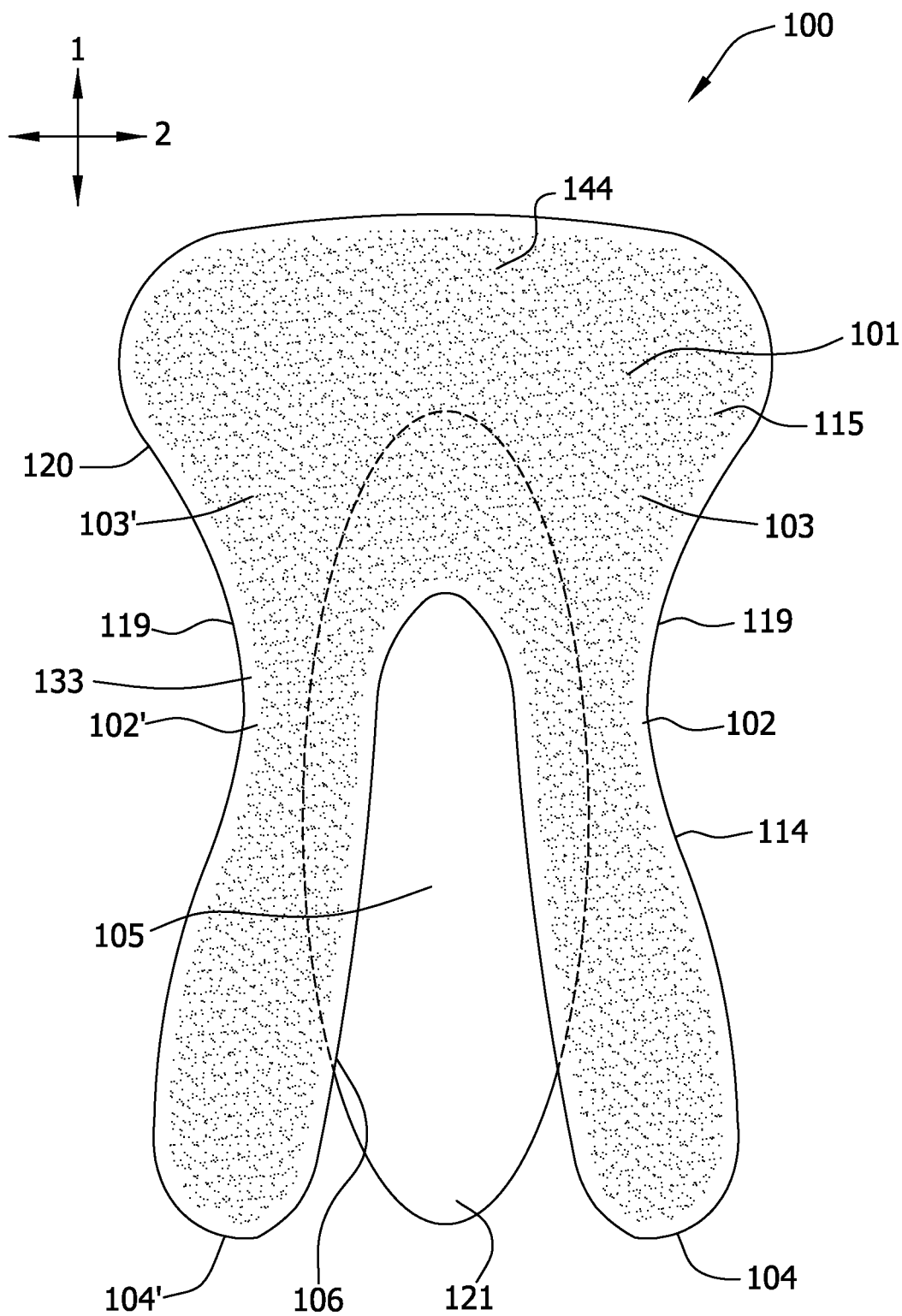
FIG. 1 shows a top view of an embodiment of an absorbent article of the present disclosure.

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

It should be understood that the term "absorbent product" or "absorbent article", as used herein, refers to any article used to control bodily fluids that are configured to absorb and retain bodily exudates, including urine, blood, menses, and other bodily discharges, such as sweat and vaginal secretions resulting from sexual activity and the like. In addition, the term is intended to include odor absorbing articles.

As used herein, the term "polymer" generally includes, but is not limited to, homopolymers, copolymers, such as, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to, isotactic, syndiotactic and random symmetries.

As used herein, "adhesion modifier" refers to an agent that allows the adhesive of the skin-adhesive composition to maintain its bonding strength with the substrate and improve its bonding strength with skin, yet remain gentle on the skin's surface. Furthermore, the adhesion modifier behaves as a delivery vehicle or carrier to aid in the delivering of one or more skin benefit agents to the skin of the user. Typically, the adhesion modifier has a polymer-like or matrix network structure that may have numerous micropores or channels, which can hold the skin benefit agent as described below. Suitable adhesive modifiers may include, for example, Polypores®, Polytraps®, and the like. Particularly suitable examples, described more fully below, include Polytrap® 7603, which is an allyl methacrylate/glycol dimethacrylate crosspolymer; Polytrap® 6603, which is a lauryl methacrylate/glycol dimethacrylate crosspolymer; Poly-Pore® E200 and Poly-Pore® L200, both of which are allyl methacrylate crosspolymers.

As used herein, "body-facing surface" means that surface of the absorbent article which is intended to be disposed toward or placed adjacent to the body or skin of the wearer during ordinary use. The "garment-facing surface" is on the opposite side of the absorbent article from the body-facing surface. The garment-facing surface is an outward surface of the absorbent article and is intended to be disposed to face away from the wearer's body during ordinary use. The garment-facing surface is generally arranged to face toward or placed adjacent to the wearer's undergarments when the absorbent article is worn.

As used herein, the term "connected" is intended to mean directly connected and indirectly connected. By directly connected, it is intended that the connected elements are in contact with one another or affixed or adhered to one another. By indirectly connected, it is intended that one or more intervening or intermediate elements are between the two elements which are secured or "connected" together. The intervening elements may be affixed or adhered.

As used herein, the term "absorbent structure" is intended to mean a configuration of an absorbent material which allows bodily fluids to be absorbed by the absorbent material.

As used herein, the term "substrate" is intended to mean any substrate known in the absorbent articles, health care products, and/or personal care product art. For example, absorbent articles can include diapers, tampons, incontinence articles, and the like. Health care products include products such as masks, surgical gowns, gloves, and the like. While described herein, as being directed to solely inanimate articles, it should be understood that in some embodiments, the substrate is the human skin of the wearer itself.

DETAILED DESCRIPTION OF THE DISCLOSURE

The present disclosure is directed to improved skin-adhesive compositions for bonding a substrate, such as an absorbent article, to skin. More particularly, the skin-adhesive composition has an improved, yet gentle, adhesion to the skin of a user. Furthermore, it has been found that the skin-adhesive composition has a stronger bonding effect to a non-skin substrate, such as the absorbent articles described below.

Generally, the skin-adhesive composition of the present disclosure includes an acrylate-based adhesive and an adhesion modifier. It has been found that the adhesion modifier can allow the adhesive to have a greater bonding strength with a substrate, yet remain gentle on the skin's surface. In one embodiment, the skin-adhesive composition can further include at least one skin benefit agent for providing improved skin health to the user.

Skin-Adhesive Compositions of the Present Disclosure

The acrylate-based adhesive may be any acrylate-based adhesive known in the art, provided that the adhesive is not a known irritant to human skin or that the adhesive is so aggressive that it causes pain to the user/wearer when the substrate or absorbent article is removed from the skin. It is also desirable that the adhesive is selected such that the adhesive does not leave a substantial amount of adhesive residue on the surface of the skin of the wearer when the substrate or absorbent article is removed by the wearer after use.

Suitable acrylate-based adhesive can typically be made from acrylate copolymers and tackifiers as known in the art. For example, typical acrylate-based adhesives include an alkyl acrylate, preferably a monofunctional unsaturated acrylate ester of a non-tertiary alkyl alcohol, wherein the alkyl group contains 1 to about 14 carbon atoms. Included within this class of monomers are, for example, isooctyl acrylate, isononyl acrylate, 2-ethylhexyl acrylate, decyl acrylate, dodecyl acrylate, n-butyl acrylate, and hexyl acrylate. In one embodiment, the acrylate-based adhesive includes acrylate-based pressure sensitive adhesives including acrylate monomers such as isooctyl acrylate, isononyl acrylate, and butyl acrylate. In another embodiment, the acrylate-based adhesives include polyacrylate hot-melt adhesives, such as the polyacrylate hot-melt adhesive, commercially available as NS 34-546B from National Starch and Chemical Company (Bridgewater, N.J.).

As noted above, the acrylate-based adhesive should form a sufficiently strong bond with the substrate or absorbent article such as to prevent premature peeling or delaminating of the substrate or absorbent article; however, the adhesive needs to remain gently attached to the skin's surface so as to be easily and comfortably removed and/or reapplied. Accordingly, the acrylate-based adhesives used in the compositions of the present disclosure provide a greater peel strength relating to the attachment between the skin-adhesive composition and the substrate (or absorbent article) than the peel strength relating to the attachment between the composition and the surface of a user's skin. Particularly, the acrylate-based adhesives should provide a skin-adhesive composition having a peel strength of composition to substrate/absorbent article of greater than about 800 grams per inch. More suitably, the peel strength of the composition to a substrate such as an absorbent article is from about 800 grams per inch to about 1500 grams per inch, and even more suitably, from about 900 grams per inch to about 1000 grams per inch.

In one or more embodiments, when the adhesive composition is applied to a body-facing surface of an absorbent article as described below to attach to a user's skin, the acrylate-based adhesives should provide the skin-adhesive composition with a high peel strength of composition to body-facing surface of the absorbent article shell, while remaining gentle on the skin's surface. Suitably, the composition has a peel strength of composition to skin of greater than about 20 grams per inch, more suitably, greater than 25 grams per inch, even more suitably, 50 grams per inch, and even more suitably, of from about 75 grams per inch to about 500 grams per inch, and even more suitably, of from about 100 grams per inch to about 200 grams per inch.

To measure peel strength of the skin-adhesive compositions, a method similar to STM 5599 may be used.

Modified STM 5599 Method—Measuring Peel Strength

Samples, being 2 inches wide and 6 inches long, are prepared. Typically the peel strength of 3 individual samples are measured, with the average of these 3 samples being reported. The reported peel strength is the average of the peak peel strength measured during an experiment.

A tensile tester is calibrated. One end of each sample is delaminated by hand so that sufficient material is present to clamp and hold the sample. For each sample, a first layer, such as a coated polyethylene film, is inserted and clamped into the upper jaw of the tensile tester. The second layer, such as a polypropylene spunbond substrate, is inserted and clamped into the lower jaw of the tensile tester. Each jaw should have a suitable facing in contact with the sample to securely hold the first or second layer without slipping or breaking as the laminate is pulled apart. The jaws of the tensile tester are initially separated by 75 mm at the start of the test. For some tests, samples are adhered to a stainless steel plate. In these cases, the sample is adhered to the stainless steel plate using a 2-kilogram roller. An exposed portion of the stainless steel plate is then clamped into the lower jaw of the tensile tester, and an exposed portion of the sample adhered to the stainless steel plate is clamped into the upper jaw of the tensile tester. Samples are then delaminated from the stainless steel plate. For peel testing off human skin (in this case the underside of a forearm without hair), a 90 degree peel test is conducted. The sample preparations are the same as the 180 degree peel test off the stainless steel plates by using the 2-kilogram roller. Typically, 3 specimens are tested for each sample.

The tensile tester is set so that the jaws move apart at a speed of approximately 12 inches per minute. The test is continued until the sample is pulled apart or until one of the layers fail. An average peel force and peak peel strength is then recorded. Different sampling rates, sampling periods, and crosshead movement durations can be used to obtain a statically valid average peel strength for samples requiring a different sample size.

After a sample delaminated or failed, the peak peel strength per unit width for each sample is calculated by dividing the peak peel strength in grams by the sample width in inches (i.e., 2 inches). Next a grand average is calculated for each sample set by averaging the three results obtained for each individual sample. The grand average for each sample set is reported in grams per inch. Suitable tensile testers for use with this test, among others, include the Sintech 2 tester, available from the Sintech Corporation, 1001 Sheldon Dr., Cary, N.C. 27513, the Instron Model™, available from the Instron Corporation, 2500 Washington St., Canton, Mass. 02021, the Thwing-Albert Model INTELLECT II, available from the Thwing-Albert Instrument Co., 10960 Dutton Rd., Philadelphia, Pa. 19154, or the MTS Alliance RT/1400, available from MTS Corporation, a business having offices in Eden Prairie, Minn.

Typically, the skin-adhesive composition of the present disclosure includes from about 40% (by total weight composition) to about 95% (by total weight composition) acrylate-based adhesive. More suitably, the skin-adhesive composition of the present disclosure includes from about 45% (by total weight composition) to about 85% (by total weight composition) acrylate-based adhesive.

In addition to the acrylate-based adhesive, the skin-adhesive composition further includes an adhesion modifier. As noted above, the adhesion modifier allows the adhesive to maintain its bonding strength with the substrate, yet remain gentle on the skin's surface. Typically, the adhesion modifier further behaves as a delivery vehicle or carrier that can aid in delivering one or more skin benefit agents to the skin of a user. For example, in one embodiment, the adhesion modifier is in the form of a matrix. The matrix-like adhesion modifier can include (i.e., be filled with) at least one skin benefit agent as described below to function as a carrier for the skin benefit agent. In this embodiment, the skin-benefit agent-containing matrix is then dispersed with the acrylate-based adhesive to form the skin-adhesive composition.

Generally, the matrix-like adhesive modifiers are channel-like matrices or pore-like matrices. Specifically, the matrix is formed in the modifiers to contain "channels" or "pores" in which the skin benefit agents can be introduced. These types of adhesive modifiers serve a dual purpose of: (1) modifying the adhesion of the skin-adhesive composition to the skin so that it can be adhered efficiently, but capable of releasing from the skin without damage to the skin; and (2) allowing for a controlled release of the skin benefit agents to the skin of the user.

It should be understood that while numerous delivery vehicles are known in the art, all delivery vehicles or carriers are not suitable for use in the skin-adhesive compositions of the present disclosure. More particularly, the adhesion modifiers must be compatible with the acrylate-based adhesive to maintain flexibility and strength of the adhesive without causing damage to the surface of the skin.

More particularly, the adhesive composition can be processed by either a hot melt process or by mixing with a solvent to form an adhesive solution. The adhesion modifier(s) can be added directly to the hot melt and as the hot melt cools, the adhesion modifier becomes suspended within the adhesive composition. Alternatively, the adhesive modifier can be added to a suitable solvent and adhesive to form a solution. In this case, the solvent will evaporate to leave the adhesion modifier suspended within the matrix of the adhesive composition. In a particularly preferred embodiment, the adhesion modifier is compatible with the solvent and the adhesion modifiers have suitable solubility within the specific solvents used with the adhesive composition. In another embodiment, the adhesion modifier does not have suitable solubility, but disperses within the solvent and the adhesive solution such that when the solvent evaporates, the adhesion modifier is suspended within the adhesive composition. Suitable solvents include, for example, acetone, methyl ethyl ketone, methyl isobutyl ketone, and ethyl acetate.

Suitable adhesion modifiers include, for example, colloidal particles, crosslinked acrylate copolymers, and combinations thereof. More particularly, colloidal particles well suited for use in the present disclosure include microcrystalline cellulose, fumed silica, silica, hydrated silica, and combinations thereof. Commercially available colloidal particles such as fumed silica (available as Cab-o-sil M5 from Cabot Corporation, Tuscola, Ill.) and blends of microcrystalline cellulose and cellulose gum (available as Avicel® 591 from FMC Corporation, Philadelphia, Pa.) are particularly suitable for use as adhesion modifiers.

In one particularly preferred embodiment, the adhesion modifier may include polymer-like network or matrix structure, such as cross-linked acrylate crosspolymers. Cross-linked acrylate crosspolymers well-suited for use in the present disclosure include allyl methacrylates crosspolymer, allyl methacrylate/glycol dimethacrylate crosspolymer, lauryl methacrylate/glycol dimethacrylate crosspolymer and derivatives thereof. Suitable examples include Poly-Pore® E-200, Poly-Pore® L-200, Polytrap® 7603 and Polytrap® 6603 Adsorber which are all available from Amcol Health & Beauty Solutions (Arlington, Ill.). The Poly-Pore® and Polytrap® ingredients can be loaded with skin beneficial ingredients prior to inclusion in the skin-adhesive combination or are available pre-loaded from Amcol Health & Beauty Solutions as Polytrap® 6035 Cyclomethicone, Polytrap® 7100 Dimethicone Macrobeads, Polytrap® 6500 Dimethicone/Petrolatum Powder, Polytrap® 665TO (which is loaded with tocopherol), and Polytrap® 6038 Mineral Oil Macrobeads.

Typically, the skin-adhesive composition of the present disclosure includes from about 1% (by total weight composition) to about 50% (by total weight composition) adhesion modifier. More suitably, the skin-adhesive composition of the present disclosure includes from about 2% (by total weight composition) to about 25% (by total weight composition) adhesion modifier, and even more suitably, from about 5% (by total weight composition) to about 20% (by total weight composition) adhesion modifier.

In one or more particularly preferred embodiments, the skin-adhesive composition further includes a skin benefit agent to provide a skin benefit (e.g., functional, aesthetic, or heath benefit) to the user/wearer. For example, as noted above, a skin benefit agent such as an antiperspirant can be beneficial to the skin-adhesive composition as it will prevent the skin-adhesive composition from weakening as a result of increased sweating in specific areas of the body for use with the skin-adhesive composition.

Exemplary skin benefit agents may include for example: antiperspirants, deodorants, skin moisturizers, humectants, pH modulators, soothing agents, antimicrobials, preservatives, film formers, and combinations thereof. Antiperspirant agents are those active ingredients generally found in antiperspirant products. In the Final Rule for U.S. Antiperspirant Drug Products for Over-the Counter Human Use; Final Monograph (68 Federal Register 34273-34293, Jun. 9, 2003) an "antiperspirant" refers to a drug product applied topically that reduces the production of perspiration (sweat) at that site. See 21 CFR 350.3 for definition and 21 CFR 350.10 for a listing of the U.S. Antiperspirant active ingredients. The following is a list of ingredients currently listed in the INCI Dictionary under this category: adipic acid/neopentyl glycol crosspolymer, aluminum chloride, aluminum chlorohydrate, aluminum chlorohydrex PEG, aluminum chlorohydrex PG, aluminum dichlorohydrate, aluminum dichlorohydrex PEG, aluminum dichlorohydrex PG, aluminum sesquichlorohydrate, aluminum sesquichlorohydrex PEG, aluminum sesquichlorohydrex PG, aluminum sulfate (aluminum sulfate buffered), aluminum zirconium octachlorohydrate, aluminum zirconium octachlorohydrex GLY, aluminum zirconium pentachlorohydrate, aluminum zirconium pentachlorohydrex GLY, aluminum zirconium tetrachlorohydrate, aluminum zirconium tetrachlorohydrex GLY, aluminum zirconium trichlorohydrate, aluminum zirconium trichlorohydrex GLY, *Bursera Graveolens* fruit oil, ferric chloride, *Humulus Lupulus* (Hops) cone extract, *Hypericum Perforatum* flower/twig extract, zirconium powder, and combinations thereof. Particularly preferred antiperspirants for use in the skin-adhesive composition of the present disclosure include commercially available REACH® Aluminum-Zirconium Complex (AZP) 908, and REACH® 103, which is a chlorohydrate, both of which are commercially available from Reheis, Inc., Berkeley Heights, N.J.

Deodorants are agents that reduce or eliminate unpleasant odors and protect against the formation of malodor on bodily surfaces. Absorbents can act as deodorants if they have the ability to absorb malodorous chemicals. Also, chemical reactions can be used to destroy the malodorous substance in selected cases. Perfumes and the like can be used to mask the perception of malodor by the process of reodorization. Unpleasant odors also may be the result of microbiological activity. Thus, cosmetic biocides are ingredients frequently used in skin-surface deodorants. The following listing of deodorants is limited to those ingredients commonly used for this purpose: adipic acid/neopentyl glycol crosspolymer, *Alpinia Uraiensis* stalk/leaf water, aluminum chloride, aluminum chlorohydrate, aluminum chlorohydrex, aluminum chlorohydrex PEG, aluminum chlorohydrex PG, aluminum dichlorohydrate, aluminum dichlorohydrex PEG, aluminum dichlorohydrex PG, aluminum lactate, aluminum phenolsulfonate, aluminum sesquichlorohydrate, aluminum sesquichlorohydrex PEG, aluminum sesquichlorohydrex PG, aluminum sulfate, aluminum triphosphate, aluminum zinc oxide, aluminum zirconium octachlorohydrate, aluminum zirconium octachlorohydrex GLY, aluminum zirconium pentachlorohydrate, aluminum zirconium pentachlorohydrex GLY, aluminum zirconium tetrachlorohydrate, aluminum zirconium tetrachlorohydrex GLY, aluminum zirconium tetrachlorohydrex PEG, aluminum zirconium tetrachlorohydrex PG, aluminum zirconium trichlorohydrate, aluminum zirconium trichlorohydrex GLY, amber powder, ammonium phenolsulfonate, ammonium silver zinc aluminum silicate, benzalkonium bromide, benzalkonium cetyl phosphate, benzalkonium chloride, benzalkonium saccharinate, benzethonium chloride, *Boesenbergia Pandurata* Rhizome extract, bromochlorophene, t-Butyl methylphenoxy phenol, calcium magnesium silicate, *Callicarpa Macrophylla* flower extract, *Candida Bombicola*/glucose/methyl rapeseedate ferment, capryloyl gold of pleasure amino acids, cetylpyridinium chloride, chlorophyllin-copper complex, chlorothymol, chloroxylenol, *Citrus Reticulata* (Tangerine) peel oil, cloflucarban, colloidal platinum, *Cuminum Cyminum* seed extract, *Curcuma Heyneana* root powder, cyclopentadecanone, dequalinium chloride, dichlorophene, dichloro-m-xylenol, dimethicone/PEG-15 crosspolymer, dipotassium capryloyl glutamate, disodium capryloyl glutamate, disodium dihydroxyethyl sulfosuccinylundecylenate, domiphen bromide, ethylhexylglycerin, fermented vegetable, hexachlorophene, hydrolyzed *Sasa Veitchii* extract, ketoglutaric acid, lauryl isoquinolinium bromide, laurylpyridinium chloride, magnesium/aluminum/zinc/hydroxide/carbonate, *mentha aquatica* water, methylbenzethonium chloride, methyl undecylenate, *Michelia Champaca* flower oil, micrococcus/hydrolyzed nonfat milk ferment, octadecenedioic acid, oligopeptide-10, *Pandanus Amaryllifolius* leaf extract, *Pelargonium Graveolens* water, phenol, *Phyllostachys Edulis* stem extract, *Piper Betle* leaf oil, polyaminopropyl biguanide stearate, potassium capryloyl glutamate, *Rosmarinus Officinalis* (Rosemary) flower extract, *saccharomyces*/persimmon fruit juice ferment extract, *Saccharomyces/Rhodobacter/Lactobacillus/Leuconostoc/Streptomyces Griseus/Aspergillus/Bacillus* ferment filtrate, *Sasa Senanensis* leaf extract, *Sasa Senanensis* leaf powder, silver copper zeolite, sodium bicarbonate, sodium capryloyl glutamate, sodium phenolsulfonate, sodium silver aluminum silicate, *Stemmacantha Carthamoides* root extract, totarol, triclocarban, triclosan, tricyclodecenyl propionate, *Urginea Maritima* tuber extract, zeolite, zinc lactate, zinc phenolsulfonate, zinc ricinoleate, zinc silicate, and combinations thereof.

Humectants are hydroscopic agents that are widely used as skin moisturizers. Their function is to prevent the loss of moisture from the skin and to attract moisture from the environment. Common humectants include, for example, glycerin, butylene glycol, betaine, sodium hyaluronate, and the like, and combinations thereof.

Soothing agents, also referred to as emollients, lubricate, sooth, and soften the skin surface. Exemplary emollients include oily or waxy ingredients such as esters, ethers, fatty alcohols, hydrocarbons, silicones, and the like, and combinations thereof.

Film formers, also referred to as skin barrier enhancers or occlusive materials, increase the water content of the skin by blocking water evaporation. These materials generally include lipids which tend to remain on the skin surface or hydrocarbons such as petrolatum and wax.

Rheology enhancers may help increase the melt point viscosity of the formulation so that the formulation readily remains on the surface of the substrate and/or laminated article and does not substantially migrate into the interior of the substrate, while substantially not affecting the transfer of the formulation to the skin. The rheology enhancers help the formulation to maintain a high viscosity at elevated temperatures, such as those encountered during storage and transportation. Additionally, rheology enhancers can influence the overall consistency and skin feel of the formulation.

Suitable rheology enhancers include combinations of alpha-olefins and styrene alone or in combination with mineral oil or petrolatum, combinations of di-functional alpha-olefins and styrene alone or in combination with mineral oil or petrolatum, combinations of alpha-olefins and isobutene alone or in combination with mineral oil or petrolatum, ethylene/propylene/styrene copolymers alone or in combination with mineral oil or petrolatum, butylene/ethylene/styrene copolymers alone or in combination with mineral oil or petrolatum, ethylene/vinyl acetate copolymers, polyethylene polyisobutylenes, polyisobutenes, polyisobutylene, dextrin palmitate, dextrin palmitate ethylhexanoate, stearoyl inulin, stearalkonium bentonite, distearadimonium hectorite, and stearalkonium hectorite, styrenelbutadiene/styrene copolymers, styrene/isoprene/styrene copolymers, styrene-ethylenelbutylene-styrene copolymers, styrene-ethylene/propylene-styrene copolymers, (styrene-butadiene) n polymers, (styrene-isoprene) n polymers, styrene-butadiene copolymers, and styrene-ethylene/propylene copolymers and combinations thereof. Specifically, rheology enhancers such as mineral oil and ethylene/propylene/styrene copolymers, and mineral oil and butylene/ethylene/styrene copolymers (Versagel blends from Penreco) are particularly preferred. Also, Vistanex (Exxon) and Presperse (Amoco) polymers are particularly suitable rheology enhancers. Other suitable examples of oil-soluble rheology enhancers include, but are not limited to, aluminum stearate, aluminum tristearate, arachidyl alcohol, arachidyl behenate, behenyl alcohol, $C_{8-22}$ alkyl acrylate/butyl dimethicone methacrylate copolymer, $C_{12-22}$ alkyl acrylate/hydroxyethylacrylate copolymer, $C_{18-38}$ alkyl, $C_{24-54}$ acid ester, $C_{20-24}$ alkyl dimethicone, $C_{24-28}$ alkyl dimethicone, $C_{30-60}$ alkyl dimethicone ceresin, cerotic acid, cetearyl alcohol, cetearyl dimethicone/vinyl dimethicone crosspolymer, cetyl alcohol, cetyl glycol, dibehenyl fumarate, hydrogenated polyisobutene, hydrogenated oils, isocetyl alcohol, isocetyl stearoyl stearate, isophthalic acid/pentaerythritol crosspolymer benzoate/isostearate, isostearyl alcohol, isostearyl stearoyl stearate, jojoba alcohol, lanolin alcohol, lanolin wax, neopentyl glycol dicaprate, neopentyl glycol dicaprylate/dicaprate, neopentyl glycol dicaprylate/dipelargonate/dicaprate, neopentyl glycol diethylhexanoate, neopentyl glycol diheptanoate, neopentyl glycol diisostearate, neopentyl glycol dilaurate, ozokerite, palm alcohol, palm kernel alcohol, paraffin, pentaerythrityl tetramyristate, pentaerythrityl tetraoleate, pentaerythrityl tetrapelargonate, pentaerythrityl tetrastearate, pentaerythrityl trioleate, silica, synthetic beeswax, synthetic candelilla wax, synthetic carnauba, vinyldimethyl/trimethylsiloxysilicate, stearyl dimethicone crosspolymer VP/eicosene copolymer and VP/hexadecene copolymer. Water soluble or water dispersable rheology modifiers include, but are not limited to, acetamide MEA, acrylamide/ethalkonium chloride acrylate Copolymer, acrylamide/ethyltrimonium chloride acrylate/ethalkonium chloride acrylate copolymer, acrylamides copolymer, acrylamide/sodium acrylate copolymer, acrylates/acetoacetoxyethyl methacrylate copolymer, acrylates/beheneth-25 methacrylate copolymer, acrylates/$C_{10-30}$ alkyl acrylate crosspolymer, acrylates/ceteth-20 itaconate copolymer, acrylates/ceteth-20 methacrylate copolymer, acrylates/laureth-25 methacrylate copolymer, acrylates/palmeth-25 acrylate copolymer, acrylates/palmeth-25 itaconate copolymer, acrylates/steareth-50 acrylate copolymer, acrylates/steareth-20 itaconate copolymer, acrylates/steareth-20 methacrylate copolymer, acrylates/stearyl methacrylate copolymer, acrylates/vinyl isodecanoate crosspolymer, acrylates/vinyl neodecanoate crosspolymer, acrylic acid/acrylonitrogens copolymer, agar, agarose, algin, alginic acid, ammonium acryloyldimethyltaurate/vinyl formamide copolymer, ammonium acryloyldimethyltaurate/VP copolymer, ammonium alginate, ammonium chloride, amylopectin, *avena sativa* (oat) kernel flour, bentonite, calcium alginate, calcium carrageenan, $C_{20-40}$ alkyl stearate, carbomer, carboxybutyl chitosan, carboxymethyl hydroxyethylcellulose, carboxymethyl hydroxypropyl guar, *cassia* Gum, cellulose gum, cetyl hydroxyethylcellulose, $C_{12-14}$ hydroxyalkyl, hydroxyethyl sarcosine, cocamide DEA, cocamide MEA, decyl HDI/PEG-180 crosspolymer, decyltetradeceth-200 isostearate, dextrin, dimethicone/PEG-10 crosspolymer, dimethicone/PEG-15 crosspolymer, dimethylacrylamide/ethyltrimonium chloride methacrylate copolymer, disteareth-75 IPDI, disteareth-100 IPDI, gelatin, gellan gum, hectorite, hydrated silica, hydrolyzed cellulose gum, hydroxybutyl methylcellulose, hydroxyethylcellulose, hydroxyethyl ethylcellulose, hydroxypropyl chitosan, hydroxypropyl guar, hydroxypropyl methylcellulose, hydroxypropyl methylcellulose stearoxy ether, hydroxypropyl starch, hydroxypropyl starch phosphate, hydroxypropyl xanthan gum, isopolyglyceryl-3 dimethicone, isopolyglyceryl-3 dimethiconol, lauryl hydroxysultaine, lauryl/myristyl glycol hydroxypropyl ether, lauryl PEG-9 polydimethylsiloxyethyl dimethicone, lauryl polyglyceryl-3 polydimethylsiloxyethyl dimethicone, levan, magnesium alginate, magnesium aluminum silicate, magnesium silicate, magnesium trisilicate, methoxy PEG-22/dodecyl glycol copolymer, methylcellulose, methyl ethylcellulose, methyl hydroxyethylcellulose, microcrystalline cellulose, montmorillonite, myristamidopropyl hydroxysultaine, oatamidopropyl betaine, octacosanyl glycol isostearate, octadecene/MA copolymer, pectin, PEG-150/decyl alcohol/SMDI copolymer, PEG-175 diisostearate, PEG-190 distearate, PEG-15 glyceryl tristearate, PEG-140 glyceryl tristearate, PEG-240/HDI copolymer bis-decyltetradeceth-20 ether, PEG-100/IPDI copolymer, PEG-180/laureth-50/TMMG copolymer, PEG-10/lauryl dimethicone crosspolymer, PEG-15/lauryl dimethicone crosspolymer, PEG-2M, PEG-5M, PEG-7M, PEG-9M, PEG-14 MPEG-20M, PEG-23M, PEG-25M, PEG-45M, PEG-65M, PEG-90M, PEG-115M, PEG-160M, PEG-180M, PEG-120 methyl glucose triisostearate, PEG-120 methyl glucose trioleate, PEG-150 pentaerythrityl tetrastearate, PEG/PPG-120/10 trimethylolpropane trioleate, PEG/PPG-120/10 trimethylpropane trioleatePEG-150/stearyl alcohol/SMDI copolymer, polyacrylate-3, polyacrylate-10, polyacrylate-11, polyacrylic acid, polycyclopentadiene, polyester-5, polyether-1, polyethylene/isopropyl maleate/MA copolyol, polyglycerin-20, polyglycerin-40, polyglyceryl-3 disiloxane dimethicone polyglyceryl-3 polydimethylsiloxyethyl dimethicone, polyquaternium-86, polyvinyl alcohol, potassium polyacrylate, potato starch modified, PVP montmorillonite, sodium acrylates/acrylonitrogens copolymer, sodium acrylates copolymer, sodium acrylates crosspolymer, sodium acrylate/sodium acrylamidomethylpropane sulfonate copolymer, sodium acrylate/sodium acryloyldimethyl taurate/acrylamide copolymer, sodium acrylates/vinyl isodecanoate crosspolymer, sodium acrylate/vinyl alcohol copolymer, sodium acryloyldimethyl taurate/acrylamide/VP copolymer, sodium carboxymethyl beta-glucan, sodium carboxymethyl starch, sodium carrageenan, sodium cellulose sulfate, sodium chloride, sodium hydroxypropyl starch phosphate, sodium isooctylene/MA copolymer, sodium polyacrylate, sodium silicoaluminate, sodium starch octenylsuccinate, sodium sulfate, steareth-100/PEG-136/HDI copolymer, tapioca starch, TEA-alginate, TEA-carbomer, trehalose hydroxypropyltrimonium chloride, tridecyl alcohol, undecyl alcohol, wheat germamidopropyl betaine, xanthan gum, yeast, polysaccharides, and *Zea Mays* (corn) starch.

Still other optional components that may be desirable for use with the formulation of the present disclosure include those cosmetic and pharmaceutical ingredients commonly used in the skin care industry. Examples include abrasives, absorbents, aesthetic components (fragrances, pigments, colorings/colorants), essential oils, skin sensates, astringents (e.g., clove oil, menthol, camphor, eucalyptus oil, eugenol, menthyl lactate, witch hazel distillate), anti-acne agents, anti-caking agents, antifoaming agents, antioxidants, binders, biological additives, buffering agents, bulking agents, chelating agents, chemical additives, colorants, cosmetic astringents, cosmetic biocides, denaturants, drug astringents, external analgesics, opacifying agents, propellants, reducing agents, sequestrants, skin bleaching and lightening agents (e.g., hydroquinone, kojic acid, ascorbic acid, magnesium ascorbyl phosphate, ascorbyl glucosamine), skin-moisturizing agents, skin-conditioning agents, skin soothing and/or healing agents (e.g., panthenol and derivatives thereof, aloe vera, pantothenic acid and derivatives thereof, allantoin, bisabolol, dipotassium glycyrrhizinate), skin treating agents, sunscreens, thickeners, and vitamins, and combinations thereof. Examples of these and other agents are disclosed in The CTFA Cosmetic Ingredient Handbook, $12^{th}$ Ed. (2007), which is hereby incorporated by reference to the extent that it is consistent herewith.

The amounts of the optional components will depend on types the acrylate-based adhesive and adhesion modifier used and the amounts of these components as well as the desired benefits of the formulations. Typically, the skin-adhesive composition will include from about 0.001% (by total weight composition) to about 60% (by total weight composition) skin benefit agent. More suitably, the skin-adhesive composition will include from about 0.01% (by total weight composition) to about 30% (by total weight composition) skin benefit agent, and even more suitably, from about 0.01% (by total weight composition) to about 20% (by total weight composition) skin benefit agent.

The skin-adhesive composition can be in the form of a single layer or multi-layer composition. For example, in one embodiment, the skin-adhesive composition is a single layer embodiment. More particularly, as noted above, the adhesion modifier is a matrix or a polymer-like network, optionally filled with at least one skin benefit agent, and then uniformly dispersed within the acrylate-based adhesive to form the single layer. It should be recognized by one skilled in the art that more than one skin benefit agent can be used in this embodiment.

Representative Substrates and Absorbent Articles for Use with the Skin-Adhesive Compositions The skin-adhesive compositions can be used with substrates and absorbent articles. Particularly, while described in terms of using the skin-adhesive composition with an absorbent article, it should be recognized that the skin-adhesive composition can be used with any of the substrates used for the components of the absorbent article, or any other substrate known in the personal care art.

The absorbent article of the present disclosure is designed to adhere to the body of a wearer in the area of the body of the wearer which may need bodily fluids absorbed. In one particular use of the absorbent article, the absorbent article is attached to the body of a female wearer to or around the vulva region of the body. By "to or around the vulva region", it is meant adjacent regions of the body of a female including the pubic region and the perinea region. When applied to or around the vulva region of the female body, the absorbent article may be used as a panty-liner, sanitary napkin or incontinence article. In addition, the absorbent article may be worn as an underwear substitute since the absorbent article of the present disclosure does not need underwear to hold the absorbent article in place. As an underwear substitute, the absorbent article provides protection to the vulva area by creating a barrier between the outer clothing and the vulva of a wearer. When worn as an underwear substitute, the absorbent article serves to protect the outer clothing of the wearer from bodily discharges from the vulva region of the wearer's body. In addition, when the absorbent article is worn as an underwear substitute, the absorbent article also serves to protect the sensitive skin and body features of the vulva region from roughness of the outer clothing, thereby preventing or alleviating irritation to the sensitive skin and body features of the vulva region. While described herein as a female personal article such as a panty-liner or sanitary napkin, it should be recognized by one skilled in the art that the absorbent article can be any absorbent article in the personal care art, and further, the user need not be a female.

Figure 2:
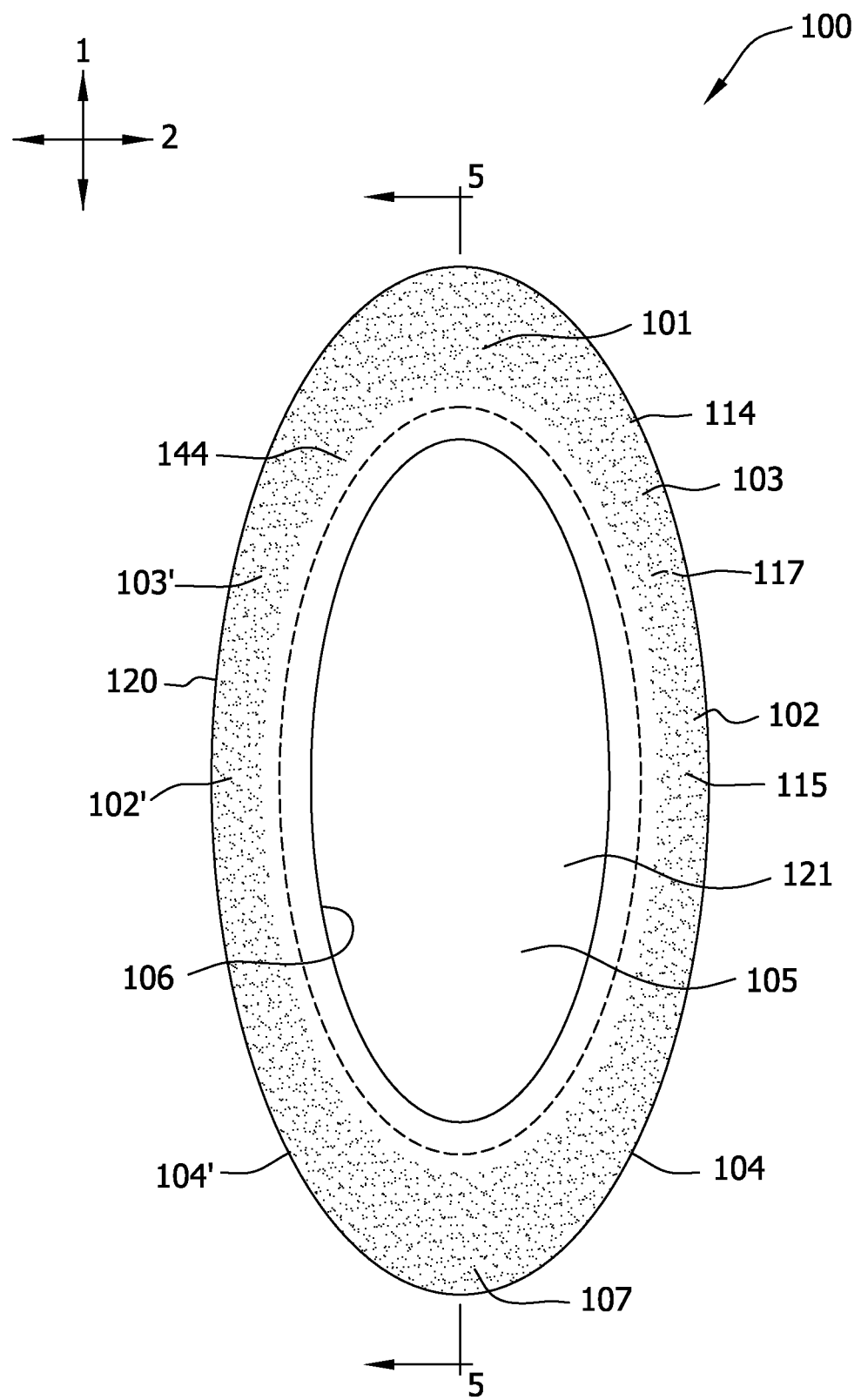
FIG. 2 shows a top view of an embodiment of an absorbent article of the present disclosure.
Figure 3:
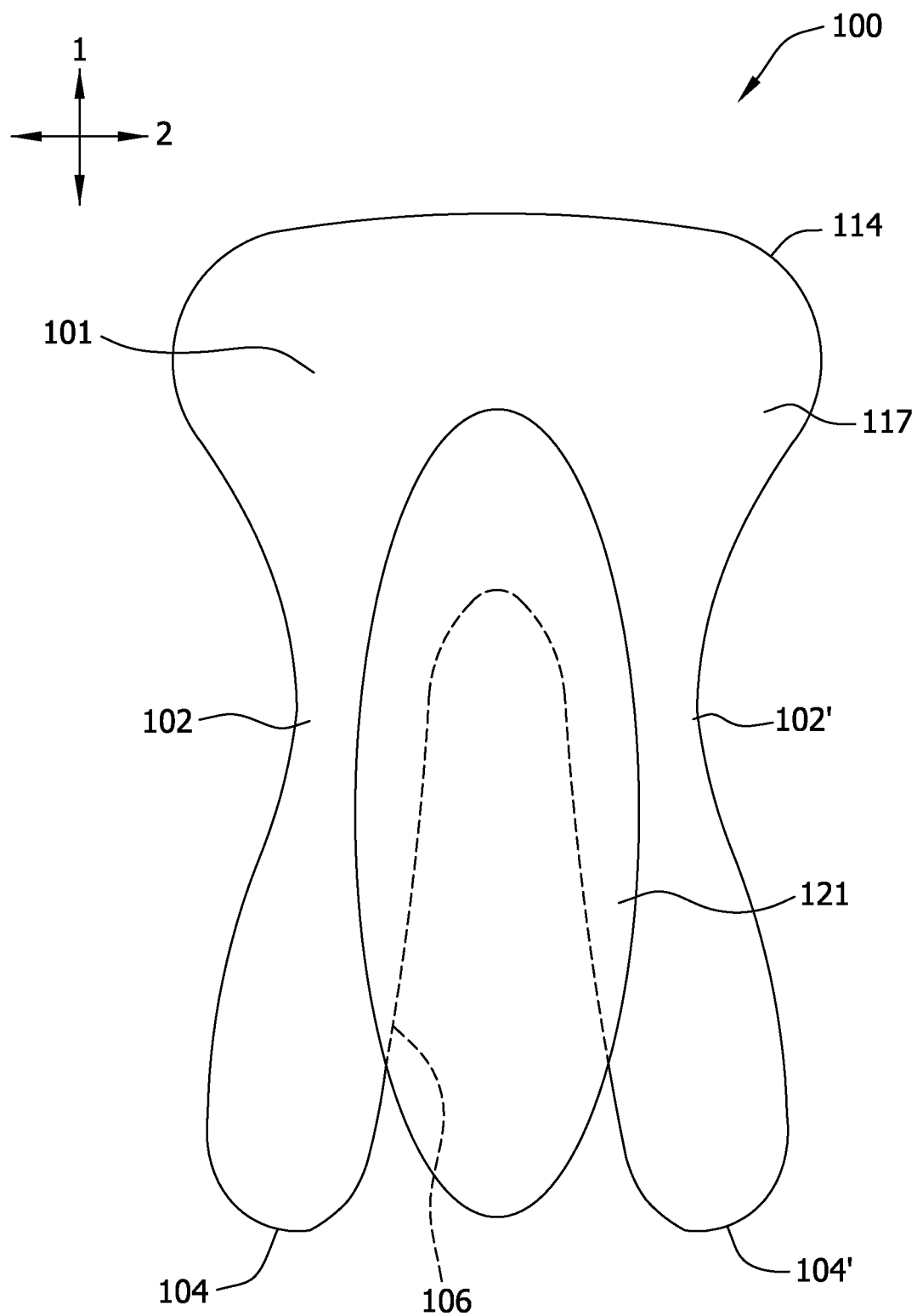
FIG. 3 shows a bottom view of the absorbent article shown in the embodiment of absorbent article of the present disclosure shown in FIG. 1.
Figure 4:
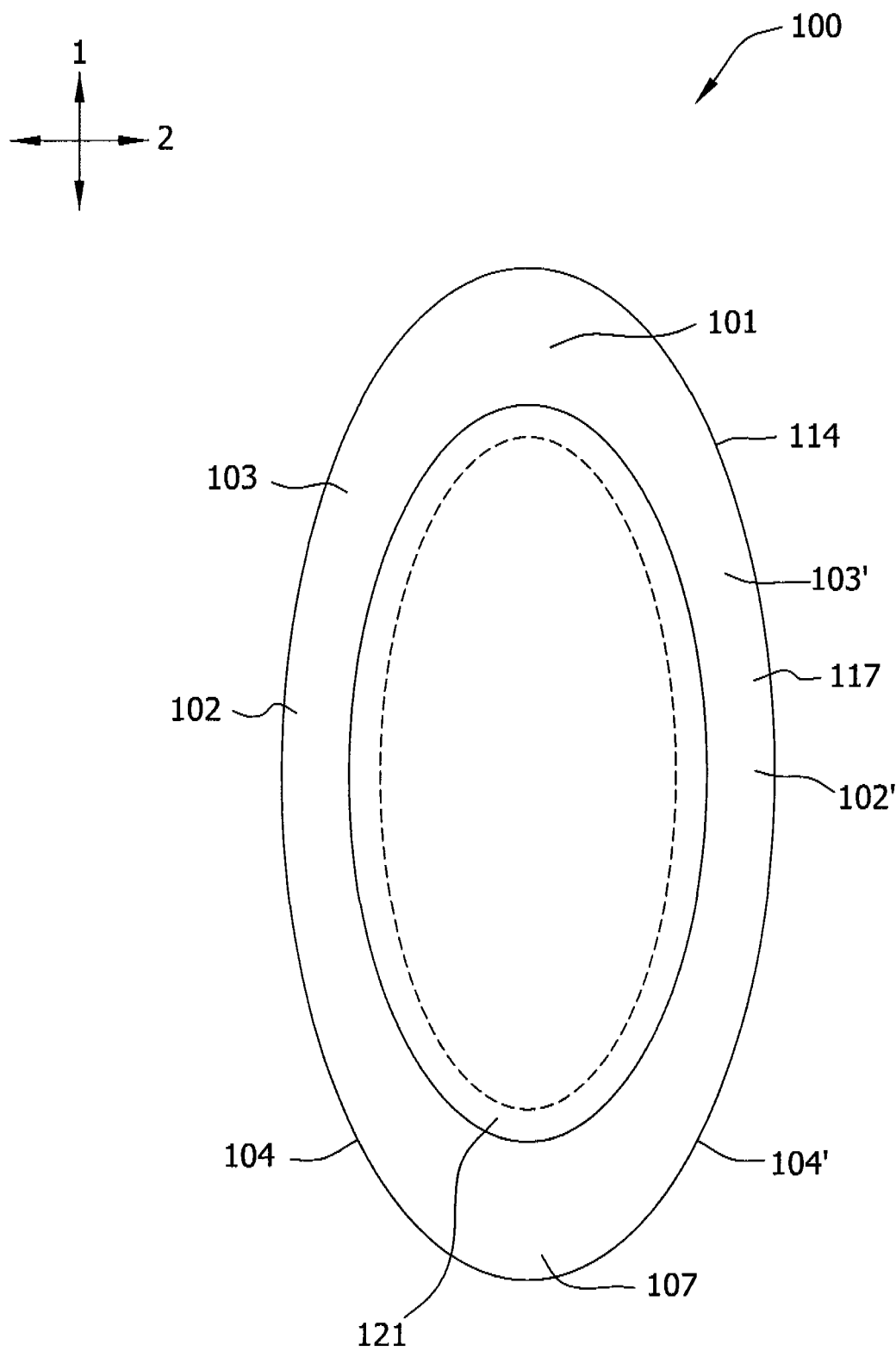
FIG. 4 shows a bottom view of the absorbent article shown in the embodiment of absorbent article of the present disclosure shown in FIG. 2.

To gain a better understanding of the present disclosure, attention is directed to the Figures of the present specification. As is shown in each of the Figures, in particular FIGS. 1 and 2, the absorbent article 100 has a longitudinal direction 1 and a lateral direction 2. One component of the absorbent article 100 is a shell 114. This shell 114 has a first side 115, as shown in FIGS. 1 and 2, and a second side 117, as is shown in FIGS. 3 and 4. The shell 114 serves to provide the overall contour or silhouette of the absorbent article of the present disclosure. In addition, the shell 114 also provides a surface for attachment or adhesion of the absorbent article 100 to the body of a wearer.

The first side 115 of the shell 114 is the body facing side of the absorbent article 100 and the second side 117 of the shell 114 is the garment facing side of the absorbent article. The shell 114 of the absorbent article 100 has a first region 101. This first region 101 has a pair of lateral side regions 102, 102' extending from the first region. This pair of lateral side regions each has a proximate end 103, 103' adjacent the first region 101 and a distal end 104, 104'. The pair of lateral side regions 102, 102' and the first region 101 together define an opening 105 in the shell 114. This opening 105 may be open near the distal ends 104, 104' of the lateral side regions 102, 102', as is shown in FIG. 1 or, as shown in FIG. 2, the lateral side regions 102, 102' may be joined at the distal end 104, 104' to form a second region 107. The portions of the lateral side regions 102, 102' and the first region 101 adjacent the opening 105 form a circumference or edge 106 around the opening 105. This circumference or edge 106 typically has thickness in the z-direction 3 which is about equal to the thickness of the shell. However, the thickness of the edge may be increased or decreased to improve comfort for a wearer or performance of the absorbent article.

The absorbent article 100 further has an absorbent structure 121 attached to the second side 117 of the shell 114, as is shown in FIGS. 1-6. At least a portion of the absorbent structure 121 is positioned in the absorbent article such that a majority of the opening 105 in the shell has the absorbent structure 121 positioned therein, as can be seen in FIGS. 1 and 2. In one particular embodiment, the entire area of the opening 105 has the absorbent structure 121 positioned therein. Generally to hold the absorbent structure in place, a portion of the absorbent structure 121 is attached to the second side 117 of the shell 114. Suitable methods of attaching the absorbent structure 121 to the second side 117 of the shell 114 includes adhesives and mechanically bonding of the absorbent structure 121 to the second side 117 using bonding means such as ultrasonic bonding, heat and pressure bonding and the like.

In one embodiment of the present disclosure, the opening 105 in the shell may be a hole, which is devoid of any material, or, and in another embodiment of the present disclosure, the opening 105 may be a region which is permeable to body fluids. If the opening is a region which is permeable, the opening may have a material such as hydrogel or similar material that will allow body fluids to flow through the material.

In one embodiment, the first side 115 of the shell 114 is adapted to be the body contacting side of the absorbent article. The first region 101, the lateral side regions 102, 102' and the second region 107, when present, on the first side 115 of the shell 114 are designed or adapted to adhere to the wearer's skin.

Generally, the shell 114 is sized and shaped such that the extent of the first side 115 of the shell 114 only contacts or adheres to the skin surrounding and proximate to the vulva area and possibly the pubic and perinea regions of the wearer. The first side 115 of the shell 114 is what holds the absorbent article in place on the body of a wearer.

The shell 114 of the absorbent article 100 may be prepared from a variety of materials. The shell may include a layer constructed of any material which will function to be operatively liquid impermeable. The shell 114 may, for example, include a polymeric film, a woven fabric, a nonwoven fabric or the like, as well as combinations or composites thereof. For example, the shell 114 may include a polymer film laminated to a woven or nonwoven fabric. A laminate shell 114 structure is shown in FIG. 6, having an upper layer 141 and a lower layer 142, wherein the upper layer 141 is the body-facing side of the shell 114 and the lower layer 142 is the garment facing side of the shell 114. In a particular embodiment, the polymer film can be composed of polyethylene, polypropylene, polyester, silicone or the like, as well as combinations thereof. Additionally, the polymer film may be micro-embossed, have a printed design, have a printed message to the consumer, and/or may be at least partially colored. Suitably, the shell 114 can operatively permit a sufficient passage of air and moisture vapor out of the absorbent article 100, particularly out of an absorbent structure 121 while blocking the passage of bodily fluids and odors often associated with bodily fluids. An example of a suitable shell material can include a breathable, microporous film, such as those described in, for example, U.S. Pat. No. 6,045,900 to Haffner et al., the entire disclosure of which is incorporated herein by reference to the extent that it is consistent herewith. Other shell materials which are extensible may be used in the present disclosure, including, for example foams. One example of a suitable foam is a polyurethane foam with a negative Poissons ratio. Examples of extensible backsheet materials are described in U.S. Pat. No. 5,611,790, issued Mar. 18, 1997, to Osborn, III et al., herein incorporated by reference to the extent that it is consistent herewith. Other materials that are inherently breathable, such as polyurethanes, may be used to form the shell 114.

In one particular embodiment of the present disclosure, the shell 114 may be a laminate of a woven or nonwoven fabric with a silicone polymer. The second side 117 of the shell will be woven or nonwoven fabric and the first side 115 of the shell will be silicone polymer. One commercially available laminate is an Oleeva Fabric® 1 available from Bio Med Sciences, Inc., which have offices at 7584 Morris Court, Suite 218 Allentown, Pa. 18106. The Oleeva Fabric® is a silicone sheeting having adhesive properties laminated to a fabric backing. The silicone sheeting will form the body facing first side 115 of the shell material. Relating this particular structure to the Figures, in FIG. 6, the silicone polymer is the upper layer 141 of the shell 114 and the nonwoven or woven layer is the lower layer 142 of the shell.

Bicomponent films or other multi-component films can also be used as the shell 114 material. In addition, woven and/or nonwoven fabrics which have been treated to render them operatively liquid-impermeable can also be used as an effective shell 114 material. Another suitable shell material can include foams. Examples of foam include a closed-cell polyolefin foam, a foam with a negative Poissons ratio and other similar foams. Other suitable polymeric materials include a polyurethane polymer material, a silicone polymer or other similar materials.

In another embodiment of the present disclosure, the shell material may be prepared from an interpenetrating polymer network or two or more polymers. Generally, one of the polymers of the interpenetrating polymer network may be a silicone material. Examples of interpenetrating polymer networks are described in U.S. Pat. No. 5,759,560, issued to Dillion, which is hereby incorporated by reference to the extent that it is consistent herewith.

The shell material should be selected such that the overall properties of the shell allow the shell material to move with the skin of the wearer during normal use and normal movements by the wearer during use. By "normal movement by the wearer" it is meant any movement that normally occurs during use of the absorbent article, including walking, running, sitting, standing, kneeling, riding a bicycle, exercising, playing sports, getting into and out of an automobile, and other similar movements made by wearers when wearing an absorbent article. The shell should not be too rigid, such that the shell detaches from the skin of the wearer during use and the shell should not be so flexible that the shell tends to twist and bunch during use. The shell should have sufficient flexibility to conform to the skin of the wearer and become similar to a second skin of the wearer. The shell should also have the ability to remain attached to the body of the wearer under moist or wet conditions.

Generally, the shell material should have sufficient thickness to allow the shell 114 to mold to the body of the wearer, but not too thick that the shell 114 becomes uncomfortable for the wearer to wear. In addition, the shell 114 should not be so thin that it ineffectively forms a seal with the skin of the wearer when applied to the wearer, or becomes detached from the skin of the wearer during use and normal movement of the wearer during use or that it does not adequately conform to the shape and skin of the wearer at the point of attachment to the wearer. Depending on the material used for the shell, the typical thickness of the shell is between 0.03 mm and about 5.0 mm, more particularly between 0.1 mm and 3.0 mm. In one particular embodiment, the thickness of the shell is between 0.25 mm and about 3.0 mm. Again, the actual thickness used is dependent of several factors including rigidity of the material, the flexibility of the material and the ability of the material to assume the shape of the skin of the wearer at the location of use.

The second side 117 of the shell 114 may form a portion of the garment-facing side of the absorbent article 100 when worn by a wearer. The shell material should be selected such that the second side 117 of the shell will freely move against the undergarment or clothing of a wearer. One way to achieve this result is to construct the second side 117 of the shell 114 to have a fairly low coefficient of friction. This will allow the second side 117 of the shell 114 to freely move against the undergarment or other clothing worn by the wearer. If the second side 117 of the shell 114, does not freely move against the undergarment or other clothing worn by the wearer, the absorbent article may catch on the undergarment or clothing, which may result in the absorbent article being prematurely and undesirably removed from the wearer or may cause the absorbent article to be shifted from its desired placement against the body of a wearer.

In order to achieve the desired coefficient of friction on the second side 117 of the shell 114, the materials used to prepare the shell could be selected such that the second side 117 of the shell material will inherently have the desired coefficient of friction. Alternatively, the second side 117 of the shell 114 may be treated with a coating composition, such a polytetrafluoroethylene-containing coating, a silicone-containing coating or other similar coating having low coefficient of friction properties. Alternatively, the shell 114 could be made from a laminate of two or more materials such that the first side 115 of the shell 114 is prepared from a material which meets the needed properties of the first side 115, while the material selected for the second side 117 of the shell 114 meets the desired coefficient of friction such that the second side 117 will move freely against the undergarment or garment being worn by a wearer.

Figure 5:
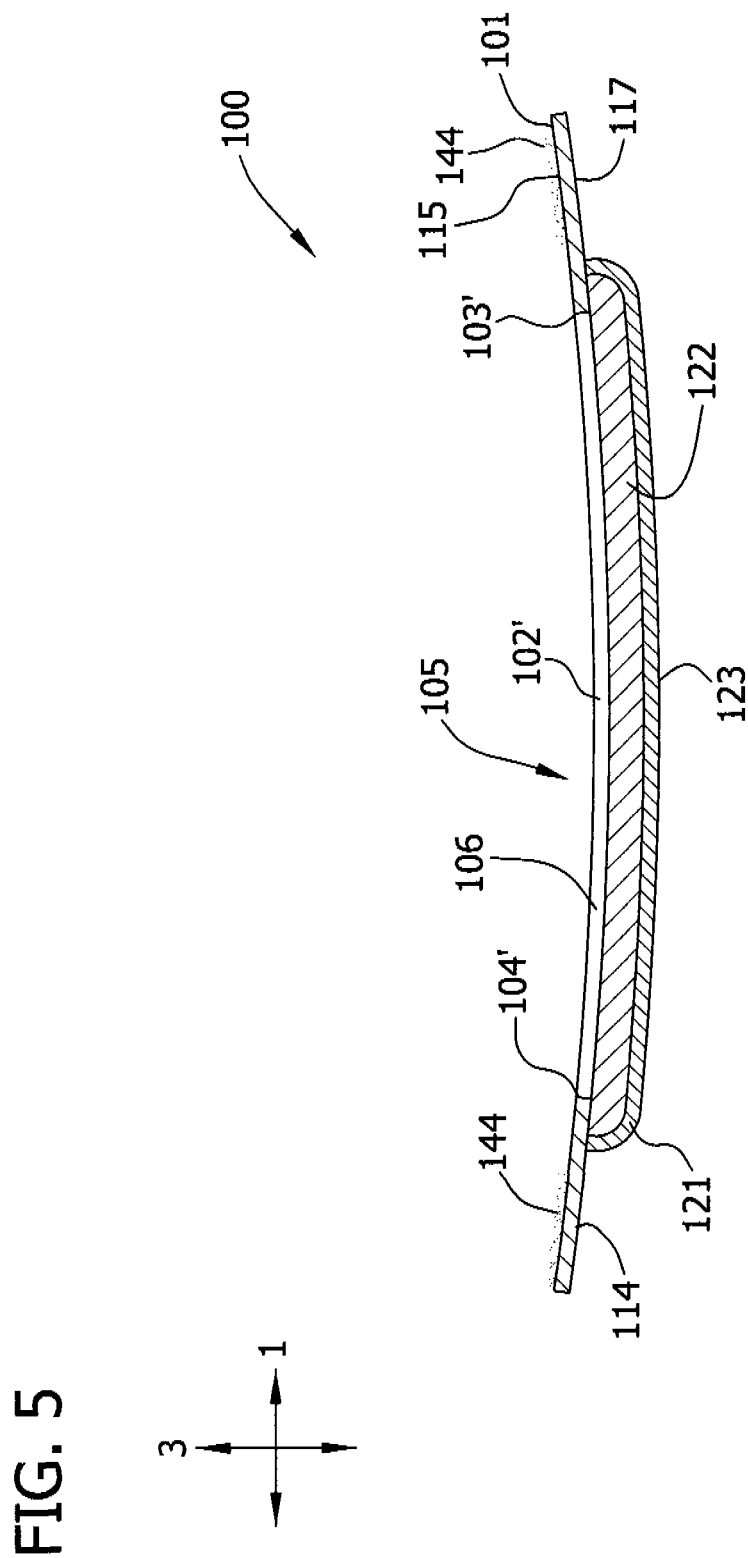
FIG. 5 shows a side cut-away view of an embodiment of an absorbent article of the present disclosure shown in FIG. 2 along line 5-5.

The shell 114 of the absorbent article 100 may be flat or may have a three-dimensional shape. As is shown in FIG. 5, which is a cross-sectional side view of the absorbent article, the shell 114 has a three-dimensional concave shape. Alternatively, as is shown in cross-sectional side views of FIG. 6, the shell 114 may have a generally flat shape. By providing the absorbent article 100 with a three-dimensional concave shape, as is shown in FIG. 5, placement of the article may be easier for the wearer. Generally, the three-dimensional shape could be such that it closely matches the overall general curvature of the vulva region and optionally the pubic and perinea regions of most women, when the absorbent article is used as a panty-liner, sanitary napkin or a feminine incontinence article. To form the shell 114 with a three-dimensional shape, the shell may be molded in any manner known to those skilled in the art, for example heat molding. The manner in which the three-dimensional shape is imparted to the shell 114 is not critical to the present disclosure.

When the shell 114 is a generally flat shape, for example as shown in FIG. 6, meaning that the shell does not have a third dimension other than thickness, the shell 114 should be made to be flexible enough that the shell 114 can conform to the body of the wearer at the point of attachment. In addition to being flat, the overall shape of the shell 114 may be contoured, as is shown in FIG. 1. In one embodiment, the contour shape may be such that the narrowest point of the contour is in the crotch area of the shell 114 nearest the vulva region, as is shown in FIG. 1. The contour shape shown in FIG. 1 is one of many possible shapes, in which the shell 114 and absorbent article may be prepared. Other shapes may be used, without departing from the scope of the present disclosure. Generally, the shape selected should be such that the shell 114 and absorbent article 100 are comfortable for the wearer to wear, while providing leakage protection to the wearer. It is noted that a contour shape may also be used in conjunction with a three-dimensional shell.

The shell may be any desired color or may be translucent. In addition, the shell may have a matte finish, satin finish or a smooth finish. The particular finish color or translucency can be a matter of choice for the manufacturer of the absorbent article of the present disclosure. However, providing a shell which is translucent may assist the wearer in placing the absorbent article 100 prior to use, since the wearer may be able to see where the article is placed compared to the genitalia of the wearer.

The absorbent structure 121 is designed to absorb body exudates, including menstrual fluid, blood, urine, and other bodily fluids, such as sweat and vaginal discharges. The absorbent structure 121 has a longitudinal direction 1 and a lateral direction 2 and is shown in FIGS. 1-4, and a thickness in the z-direction 3, as is shown in FIGS. 5 and 6. This absorbent structure 121 may be a single layer or may be multiple layers. Typically, the absorbent structure 121 has an absorbent core 122 and a generally liquid impermeable backsheet 123. This absorbent core 122 may contain one or more layers of absorbent materials; that is, the absorbent core 122 may be a single layer of absorbent materials or may be a multi-layer structure. Each of the layers of the absorbent core 122 can contain similar materials or different materials. In the absorbent article 100 of the present disclosure, the materials which may be used to form the absorbent core 122 include those materials conventionally used in absorbent articles and includes materials, such as, for example, cellulose, wood pulp fluff, rayon, cotton, and meltblown polymers such as polyester, polypropylene or coform. Coform is a meltblown air-formed combination of meltblown polymers, such as polypropylene, and absorbent staple fibers, such as cellulose. A desired material is wood pulp fluff, for it is low in cost, relatively easy to form, and has good absorbency.

The absorbent core 122 can also be formed from a composite comprised of a hydrophilic material which may be formed from various natural or synthetic fibers, wood pulp fibers, regenerated cellulose or cotton fibers, or a blend of pulp and other fibers. One particular example of a material which may be used as the absorbent core is an airlaid material. The absorbent core 122 may have other properties including extensibility, which will allow the absorbent core to be extended or fit to a particular wearer. One example of extensible absorbent cores is described in U.S. Pat. No. 5,611,790, issued Mar. 18, 1997, to Osborn, III et al., herein incorporated by reference to the extent that it is consistent herewith.

In one embodiment, the absorbent core 122 may also include a superabsorbent material, in addition to or in place of the hydrophilic material, which increases the ability of the absorbent core to absorb a large amount of fluid in relation to its own weight. Generally stated, the superabsorbent material can be a water-swellable, generally water-insoluble, hydrogel-forming polymeric absorbent material, which is capable of absorbing at least about 15, suitably about 30, and possibly about 60 times or more its weight in physiological saline (e.g., saline with 0.9 wt % NaCl). The superabsorbent materials can be inserted as particles or in sheet form. The superabsorbent material may be biodegradable or bipolar. The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers may be lightly crosslinked to render the material substantially water insoluble. Crosslinking may, for example, be by irradiation or covalent, ionic, Van der Waals, or hydrogen bonding. Hydroxyfunctional polymers have been found to be good superabsorbents for sanitary napkins. Such superabsorbents are commercially available from Dow Chemical, Hoechst-Celanese, and Stockhausen, Incorporated, among others, and are a partially neutralized salt of cross-linked copolymer of polyacrylic acid and polyvinyl alcohol having an absorbency under load value above 25 grams of absorbed liquid per gram of absorbent material (g/g). Other types of superabsorbent materials known to those skilled in the art can also be used.

Selection of the actual materials used for the absorbent core 122 is within the skill of those skilled in the art. The actual materials used for the absorbent core are not critical to the present disclosure.

The generally liquid impermeable backsheet 123 is present in the absorbent structure 121 to prevent fluid entering the absorbent core 122 from flowing through the absorbent core 122 and onto a garment or undergarment being worn by a wearer. Suitable liquid impermeable backing sheets include, for example, a polymeric film, a woven fabric, a nonwoven fabric or the like, as well as combinations or composites thereof. Generally, any material that may be used as the shell material describe above may be used as the backsheet 123 of the absorbent structure 121. The liquid impermeable backsheet 123 may be a polymeric film, a woven fabric, a nonwoven fabric or the like, as well as combinations or composites thereof. For example, the liquid impermeable backsheet 123 may include a polymer film laminated to a woven or nonwoven fabric. In a particular feature, the polymer film can be composed of polyethylene, polypropylene, polyester, silicone or the like, as well as combinations thereof. Additionally, the polymer film may be micro-embossed, have a printed design, have a printed message to the consumer, and/or may be at least partially colored. Suitably, the liquid impermeable backsheet 123 can operatively permit a sufficient passage of air and moisture vapor out of the absorbent article 100, particularly out of an absorbent structure 121 while blocking the passage of bodily fluids and odors often associated with bodily fluids. An example of suitable materials for the liquid impermeable backsheet 123 can include a breathable, microporous film, such as those described in, for example, U.S. Pat. No. 6,045,900 to Haffner et al., the disclosure of which is incorporated herein by reference and made a part hereof to the extent that it is consistent herewith.

The side of the backsheet 123 which faces the undergarment or garments of a wearer should have a low coefficient of friction for the same reasons that the second side 117 of the shell should have a low coefficient of friction. This will allow the garment facing side of the backsheet 123 to move freely against the undergarment or clothing of a wearer. If the garment facing side of the backsheet 123 does not freely move against the undergarment or other clothing worn by the wearer, the absorbent article may catch on the undergarment or clothing, which may result in the absorbent article or the absorbent structure being prematurely and undesirably removed from the wearer or may cause the absorbent article to be shifted from its desired placement against the body of a wearer. In addition by having both the garment facing side of the backsheet 123 and the second side 117 of the shell freely move against the undergarment or clothing of the wearer, the body attached absorbent article will be comfortable for a wearer to wear and may provide improved protection since the undergarment or clothing will not cause the absorbent article to shift during use.

Generally, the absorbent structure will be positioned adjacent to the second side 117 of the shell 114, as can be clearly seen in FIGS. 1-6. By "adjacent to the shell", it is meant that the that the absorbent structure 121 is directly in contact with the second side 117 of the shell 114 or may be separated by one or two additional layers or a construction or pressure sensitive adhesive. The absorbent structure should be positioned such that the absorbent core 122 is beneath the opening 105 so that any fluid flowing through the opening 105 will come into contact with the absorbent core 122.

In addition to the absorbent core 122, the absorbent structure 121 may have other additional layers which aid the absorbent core 122 in capturing and holding the bodily fluid into the absorbent core 122. These other layers, when present and in combination with the absorbent core 122, form the absorbent structure 121 of the absorbent article 100. There may be a single layer or multiple layers in addition to the absorbent core 122 in the absorbent structure 121.

One particular example of an additional layer which may be used in addition to the absorbent core 122 in the absorbent structure 121 is a top sheet (not shown), which is generally a liquid permeable material, which allows bodily fluids to pass through the top-sheet into the absorbent core. The top sheet also may provide a wearer with a dry feeling by separating the absorbent core 122 from the body of the wearer. That is, the top sheet is placed between the absorbent core 122 and the body of the wearer and such that the absorbent core 122 is between the top sheet and the shell 114.

Optionally, the top sheet may be formed from one or more materials. The top sheet should be able to manage different body excretions depending on the type of product. In feminine care products, often the top sheet must be able to handle menses and urine. In addition, the top sheet may be comfortable, soft and friendly to the wearer's skin. In the present disclosure, the top sheet may include a layer constructed of any operative material, and may be a composite material. For example, the top sheet can include a woven fabric, a nonwoven fabric, a polymer film, a film-nonwoven fabric laminate or the like, as well as combinations thereof. Examples of a nonwoven fabric useable in the top sheet include, for example, an airlaid nonwoven web, a spunbond nonwoven web, a meltblown nonwoven web, a bonded-carded web, a hydroentangled nonwoven web, a spunlace web or the like, as well as combinations thereof. Other examples of suitable materials for constructing the top sheet can include rayon, bonded-carded webs of polyester, polypropylene, polyethylene, nylon, or other heat-bondable fibers, finely perforated film webs, net-like materials, and the like, as well as combinations thereof. These webs can be prepared from polymeric materials such as, for example, polyolefins, such as polypropylene and polyethylene and copolymers thereof, polyesters in general including aliphatic esters such as polylactic acid, nylon or any other heat-bondable materials. When the top sheet is a film or a film laminate, the film should be apertured or otherwise be made to allow fluids to flow through the top sheet to the absorbent core.

Other examples of suitable materials for the top sheet are composite materials of a polymer and a nonwoven fabric material. The composite materials are typically in the form of integral sheets generally formed by the extrusion of a polymer onto a nonwoven web, such as a spunbond material. In a particular arrangement, the top sheet can be configured to be operatively liquid-permeable with regard to the liquids that the article is intended to absorb or otherwise handle. The operative liquid-permeability may, for example, be provided by a plurality of pores, perforations, apertures or other openings, as well as combinations thereof, which are present or formed in the liner or body contacting layer. The apertures or other openings can help increase the rate at which bodily liquids can move through the thickness of the liner or body contacting layer and penetrate into the other components of the article (e.g. into the absorbent core 122). The selected arrangement of liquid permeability is desirably present at least on an operative portion of the top sheet that is appointed for placement on the body-side of the article. The top sheet can provide comfort and conformability, and can function to direct bodily exudates away from the body and toward the absorbent core 122. The top sheet -4 can be configured to retain little or no liquid in its structure, and can be configured to provide a relatively comfortable and non-irritating surface next to the body tissues of a wearer. In the present disclosure, the top sheet positioned over the absorbent core may have a surface which is embossed, printed or otherwise imparted with a pattern.

Additional layers or substrates, including for example, the liquid acquisition and distribution layer, also referred to as a surge or transfer layer, and an optional tissue layer are also incorporated into the absorbent structure 121 of the absorbent product 100, for example, between the top sheet and the absorbent core 122. The distribution layer may be shorter than the absorbent core or have the same length as the absorbent core 122. The distribution layer serves to temporarily hold an insulting fluid to allow the absorbent core sufficient time to absorb the fluid, especially when a superabsorbent material is present.

Typically, the skin-adhesive composition 144 is positioned on the first side 115 of the shell 114. The skin-adhesive composition 144 contacts the skin and hair, if present, in the vulva region and possibly the pubic region and/or the perinea region of the wearer's body, thereby supporting and holding the absorbent article 100 against the body of the wearer during use. The skin-adhesive composition 144 can overlie a portion of the first side 115 or can overlie the first side 115 of the shell 114. Generally, the skin-adhesive composition 144 will be present on at least the outer portion first side of the shell near the edge 120 of the absorbent article 100. The skin-adhesive may cover the entire first side 115 of the absorbent article (not shown in the drawings). Alternatively, the skin-adhesive composition 144 may be placed on a portion of the first side, as is shown in FIGS. 1 and 2. The skin-adhesive composition 144 may also be placed in a pattern of the first side 115 of the absorbent article. The skin-adhesive composition 144 can be applied to the first side 115 of the shell 114 of using any known process including inkjet printing, screen printing or extruding the skin-adhesive composition 144 from one or more nozzles, slot coating and the like.

The skin-adhesive composition 144 may be positioned on the first side 115 of the shell 114 in an open pattern or a closed pattern. By "open pattern" is meant that the adhesive can have an intermittent or discontinuous pattern which does not substantially encircle the entire opening 105. For example, there may be breaks in the skin-adhesive composition at certain portions of the first side 115. "Closed pattern" means the adhesive composition 144 would encircle the entire opening 105 in the shell. In one embodiment, the pattern of the skin-adhesive composition 144 will substantially surround the cover of the first side 115 and substantially surround the opening 105. An example of an "open" pattern of the adhesive composition would be to have individual beads of adhesive composition applied in a discontinuous fashion. In the present disclosure, the closed pattern can be advantageous since the skin-adhesive composition 144 may form a seal with the skin of the wearer which will assist in preventing leaks from the absorbent article 100. The skin-adhesive composition may form a dam, which may prevent leaks from the entire perimeter of the absorbent article 100.

In one embodiment of the present disclosure, the skin-adhesive composition 144 may be placed on the entire first side 115 of the shell 114, as is shown in FIG. 1. In another alternative embodiment of the present disclosure, as is shown in FIG. 2, the skin-adhesive composition 144 may placed along the outer portions of the first side 115 near the periphery of the shell 114, such that no adhesive composition is near the opening 105. The skin-adhesive composition 144 may also be placed on the absorbent structure 121 positioned on the second side 117 of the shell 114 to help hold the absorbent article in place on the wearer. Generally, however, the skin-adhesive composition 144 is confined to being placed on the first side 115 of the shell 114, since placing the skin-adhesive composition on an area of the absorbent product 100 which contacts the female genitalia such as the labia majora may cause discomfort to the wearer of the absorbent product 100.

The skin-adhesive composition may be applied in a pattern of small discrete dots so as to leave numerous areas free from adhesive composition. Alternatively, the adhesive composition may be applied as a continuous bead, or may be applied as a series of semi-continuous beads. Other suitable adhesive composition patterns may be selected for applying the skin-adhesive composition 144 to the body-contacting first side 115 of the absorbent article 100. For example, adhesive composition patterns can be oval, swirls, various linear or non-linear arrays of adhesive longitudinally, and/or transversely oriented and reticulated webs having unobstructed interstices between the adhesive fibers or combinations thereof. As stated above, the adhesive composition patterns may be open or closed. The weights of adhesive compositions are limited to less than about 800 g/m$^2$, and generally less than about 400 g/m$^2$. Generally, the weight of the adhesive composition is at least 10 g/m$^2$. Typically, the adhesive composition is applied in an amount of about 10 to about 400 g/m$^2$, and more suitably, in an amount of about 30 to about 200 g/m$^2$. The limitations on the basis weight of the adhesive composition are important to provide the correct adhesive characteristics for applying directly to the wearer's vulva region and optionally the pubic and perinea regions of the wearer's body. If the basis weight is too high, the absorbent article will have a sticky feeling or otherwise uncomfortable feeling. If the basis weight of the adhesive composition is too low, there may be insufficient adhesion to the body of the wearer.

Generally, the skin-adhesive composition 144 is applied in a manner which is symmetrical about the longitudinal axis which bisects the absorbent article 100 and divides the absorbent article 100 into substantially equal portions. This symmetrical pattern provides the wearer a balanced feel when wearing the absorbent article 100. The symmetrical pattern also reduces the perception of any associated discomfort when the absorbent article 100 is removed from the body.

Having described the disclosure in detail, it will be apparent that modifications and variations are possible without departing from the scope of the disclosure defined in the appended claims.

EXAMPLES

The following non-limiting examples are provided to further illustrate the present disclosure.

Example 1

In this Example, various skin-adhesive compositions were prepared and visually evaluated. More particularly, the skin-adhesive compositions were compared to two adhesive control samples containing no adhesion modifier.

To prepare the control samples, acrylate hot melt adhesive (having 50% by weight acrylate), available as NS34-546B (commercially available from National Adhesives, Bridgewater, N.J.) was dissolved in ethyl acetate to a 50% concentration and a viscosity of approximately 200 cPs at 23° C. Additionally, a combination of AZP 908 (Reheis, Inc., Berkeley Heights, N.J.) and glycerine was added to control sample B.

To prepare the various test skin-adhesive composition samples, NS34-546B (adhesive composition commercially available from National Adhesives, Bridgewater, N.J.) was dissolved in a solvent, ethyl acetate, as described above and, then, an adhesion modifier was added to the solution of adhesive, along with the various skin benefit agents as shown in Table 1. One gram of the sample was placed on an aluminum Petri dish and then dried for approximately 48 hours or until the solvent is substantially evaporated therefrom. For Samples 1-6, the adhesion modifier was an allyl methyacrylate crosslinked polymer having a particle size of approximately 20 microns (commercially available as Poly-pore® E200 from Amcol Health & Beauty Solutions (Arlington, Ill.)). For Samples 7-8, the adhesion modifier was corn starch.

After several hours, and in some cases, several days, the 1-gram samples were visually observed for separation of the components of the skin-adhesive composition and tackiness. Tackiness, which is a feeling of stickiness, is determined by using finger touch and quantifying the results on a scale of from about 1 (least tacky) to 10 (most tacky). The results are shown in Table 1.

TABLE 1

| Sample | Acrylate-based Adhesive (g) | Poly-pore® E200 or Corn Starch (g) | Skin Benefit Agent (g) | Commercial Source of Skin Benefit Agent | Visual Observation (after casting and drying) |
| --- | --- | --- | --- | --- | --- |
| Control Sample A | 5.0 | 0 | 0 | — | Transparent; tackiness = 10 |
| Control Sample B | 5.0 | 0 | 0.4 g Glycerine + 0.2 g AZP 908 | AZP available from Reheis, Inc., Berkeley Heights, New Jersey | Separation; tackiness = 8-9 |
| Sample 1 | 5.0 | 0 | 0.1 gram AZP 908 | Reheis, Inc., Berkeley Heights, New Jersey | Separation of components; tackiness = 9-10 |

TABLE 1-continued

| Sample | Acrylate-based Adhesive (g) | Poly-pore® E200 or Corn Starch (g) | Skin Benefit Agent (g) | Commercial Source of Skin Benefit Agent | Visual Observation (after casting and drying) |
|---|---|---|---|---|---|
| Sample 2 | 5.0 | 0.4 | 0.6 g AZP 908 | Reheis, Inc., Berkeley Heights, New Jersey | White composition; no separation; much less tackiness as compared to control samples (i.e., tackiness = 3-4) |
| Sample 3 | 5.0 | 0.125 | 0.5 g AZP 908 | Reheis, Inc., Berkeley Heights, New Jersey | Separated after 2-4 hours; tackiness = 6-7 |
| Sample 4 | 5.0 | 0.125 | 0.5 g. REACH® 103 | Reheis, Inc., Berkeley Heights, New Jersey | Separated after 4-6 hours; tackiness = 5-6 |
| Sample 5 | 4.75 | 0.25 | 0.5 g REACH® 103 | Reheis, Inc., Berkeley Heights, New Jersey | Almost no separation after 1 week; tackiness = 4-5 |
| Sample 6 | 4.75 | 0.25 | 0.5 g AZP 908 | Reheis, Inc., Berkeley Heights, New Jersey | Some separation after 1 week; tackiness = 4-5 |
| Sample 7 | 5.0 | 0.25 | 0 | — | Precipitation of corn starch within 24 hours; tackiness = 9-10 |
| Sample 8 | 5.0 | 0.25 | 0.5 REACH® 103 | Reheis, Inc., Berkeley Heights, New Jersey | Precipitated in several hours; tackiness = 9-10 |

As shown in Table 1, Control Samples A and B, and samples lower in adhesion modifier (e.g., Samples 1, 3, and 4), separated more easily as compared to samples having higher levels of adhesion modifier (e.g., Samples 2, 5, and 6). It should be recognized that the adhesive composition should be stable; that is, should not separate. If the composition is not stable, the composition will not have a gentle effect on skin as the top layer will solely be the acrylate-based adhesive.

Furthermore, as shown in the samples using corn starch, it should be recognized that the adhesion modifier cannot simply be any thickener known in the art. More particularly, adhesion modifiers such as Poly-pore® E200 and others as described above are required for providing a gentle, yet strong adhesive bonding effect to the skin-adhesive composition.

Example 2

In this Example, three separate skin-adhesive compositions were prepared and their peel strengths were evaluated. Furthermore, visual observations were recorded. More particularly, the skin-adhesive compositions were visually evaluated for their strength in bonding to various substrates and to their gentleness on skin when the skin-adhesive compositions were applied thereto.

To prepare the skin-adhesive compositions, 10 grams acrylate-based adhesive, available as NS34-546B (commercially available from National Adhesives, Bridgewater, N.J.) was dissolved in ethyl acetate to a 50% concentration and a viscosity of approximately 200 cPs at 23° C. In some of the samples, silica gel was added as an adhesion modifier. Furthermore, in one sample, an antiperspirant, available as REACH® 103 from Reheis, Inc., Berkeley Heights, N.J., was further added to the samples.

The skin-adhesive compositions (typically, about 50-70 gsm) were applied to three different substrates; polyethylene film on spunbond non-woven (PE/SB); polyethylene film on stainless steel substrate (PE/SS); and polyethylene film on human skin. The samples, their peel strengths, and visual observations for the samples used on the various substrates are shown in Table 2.

TABLE 2

| Sample | Skin-Adhesive Composition | Substrate | Peel Strength | Visual Observation |
|---|---|---|---|---|
| A | Adhesive (50% concentration) | PE/SB | 1680 | PE film broken; adhesive bonding solely to SB |

TABLE 2-continued

| Sample | Skin-Adhesive Composition | Substrate | Peel Strength | Visual Observation |
|---|---|---|---|---|
| A | Adhesive (50% concentration) | PE/SS | 902 | Adhesion failed as most peeled from the PE substrate and remained on the SS substrate |
| A | Adhesive (50% concentration) | PE/Skin (forearm) | N/A | Too aggressive to put on skin |
| B | 10 g adhesive (50% concentration) + 0.6 g silica gel | PE/SB | 1562 | PE film broke; adhesive composition bonding solely to SB |
| B | 10 g adhesive (50% concentration) + 0.6 g silica gel | PE/SS | 855 | Adhesion failed as most peeled from the PE substrate and remained on the SS substrate |
| B | 10 g adhesive (50% concentration) + 0.6 g silica gel | PE/Skin (forearm) | 200 | Good adhesion to the skin with no skin damage |
| C | 10 g adhesive (50% concentration) + 0.6 g silica gel + 0.5 g REACH ® 103 | PE/SB | 1300 | SB failed/broke |
| C | 10 g adhesive (50% concentration) + 0.6 g silica gel + 0.5 g REACH ® 103 | PE/SS | 940 | Adhesion failed as most peeled from the PE substrate and remained on the SS substrate |
| C | 10 g adhesive (50% concentration) + 0.6 g silica gel + 0.5 g REACH ® 103 | PE/Skin (forearm) | 160 | Good adhesion to the skin with no damage to the skin |

As shown in Table 2, silica gel can be added to the adhesive to form a skin-adhesive composition having a gentle attachment to skin, but maintaining similar bonding strength when used for attaching substrates. Furthermore, through adding skin benefit agents, such as the antiperspirant, multiple skin care benefits can be expected in addition to having a means to control adhesive bonding strength to skin and substrates.

Example 3

In this Example, two skin-adhesive compositions were prepared and visually evaluated. More particularly, the skin-adhesive compositions were compared to control samples containing no adhesion modifier.

To prepare the control samples, acrylate hot melt adhesive (having 50% by weight acrylate), available as NS34-546B (commercially available from National Adhesives, Bridgewater, N.J.) was dissolved in ethyl acetate to a 50% concentration and a viscosity of approximately 200 cPs at 23° C.

To prepare the various test skin-adhesive composition samples, NS34-546B (adhesive composition commercially available from National Adhesives, Bridgewater, N.J.) was dissolved in a solvent, ethyl acetate, as described above and, then, an adhesion modifier was added to the solution of adhesive, along with the various skin benefit agents as shown in Table 3. Specifically, a 50% (by weight) adhesive solution was prepared using 15 grams of adhesive and 15 grams of ethyl acetate. Then, using this solution, 5% (by weight) solutions of each adhesion modifier were prepared by adding 0.5 grams of adhesion modifier to 9.5 grams of the 50% (by weight) adhesive solution. The mixtures were suspended, allowed to thicken slightly, and then poured into aluminum trays where they were allowed to evaporate prior to tackiness testing. More particularly, the samples were placed on aluminum Petri dishes and dried for approximately 48 hours or until the solvent is substantially evaporated therefrom. Once the solvent had evaporated off, the samples included approximately 0.5 grams of adhesion modifier and 4.75 grams of adhesive.

For Sample 1, the adhesion modifier was Polytrap® 665TO (commercially available from Amcol Health & Beauty Solutions (Arlington, Ill.), which includes 65% (by weight) tocopherol. For Sample 2, the adhesion modifier was Polytrap® 6500 (commercially available from Amcol Health & Beauty Solutions (Arlington, Ill.), which includes 70% (by weight) dimethicone/petrolatum.

The samples were visually observed for separation of the components of the skin-adhesive composition and tackiness, as described above. The results are shown in Table 3.

TABLE 3

| Sample | Acrylate-based Adhesive (g) | Adhesion Modifier (g) | Skin Benefit Agent (g) | Visual Observation (after casting and drying) |
|---|---|---|---|---|
| Control Sample 1 | 4.75 | 0 | 0 | Visual appearance is clear; tackiness = 9-10 |
| Control Sample 2 | 4.75 | 0 | 0 | Visual appearance is clear; tackiness = 8-9 |
| Sample 1 | 4.75 | 0.5 Polytrap ® 665TO | 65% (by weight Polytrap ® 665TO) tocopherol | Visual appearance is clear; tackiness = 6-7 |
| Sample 2 | 4.75 | 0.5 Polytrap ® 6500 | 70% (by weight Polytrap ® 6500) dimethicone/ petrolatum | Visual appearance is opaque to white; tackiness = 3-4 |

As shown in Table 3, Samples 1-2 show that the adhesion modifier allows for the presence of a skin benefit agent, while maintaining compatibility with the adhesive composition in that there was little to no separation, while having a sufficient tackiness for adhesion to the skin.

In view of the above, it will be seen that the several objects of the disclosure are achieved and other advantageous results attained.

As various changes could be made in the above formulations and substrates/articles without departing from the scope of the disclosure, it is intended that all matter contained in the above description shall be interpreted as illustrative and not in a limiting sense.

What is claimed is:

1. An absorbent article for attachment to a wearer's skin in the vulva region, the absorbent article comprising an absorbent structure and a shell,
the shell having a body-facing surface and a garment-facing surface, a first region having a pair of lateral side regions extending from the first region, the pair of lateral side regions each comprise a proximate end adjacent the first region and a free distal end, and the pair of lateral side regions and the first region define an opening in the shell,
the absorbent structure being adapted to be attached to the garment-facing surface of the shell such that at least a portion of the absorbent structure is positioned in the opening in the shell and a majority of the opening of the shell has the absorbent structure positioned therein, wherein the absorbent structure has an absorbent capacity,
wherein when applied to the wearer, the body-facing surface of the shell contacts the wearer's skin surrounding the vulva region and the shell is sized and shaped such that the body-facing surface of the shell only contacts the skin of the wearer proximate to the vulva region of the wearer, and
the body-facing surface having a removable and re-attachable skin-adhesive composition thereon for adhering the shell directly to a wearer, the skin-adhesive composition comprising a hot-melt acrylate-based adhesive having 50% by weight acrylate, an adhesion modifier, and a skin benefit agent, wherein the the adhesion modifier and the skin benefit agent are present in an amount of about 10% (by total weight of the composition), wherein the adhesion modifier is patricles of lauryl methacrylate/glycol dimethacrylate crosspolymer, wherein the adhesive composition is substantially free of a solvent, and wherein the adhesion modifier is a matrix filled with the skin benefit agent and the skin benefit agent-containing matrix is dispersed within the acrylate-based adhesive to form a single layer adhesive composition.

2. The absorbent article as set forth in claim 1 wherein the adhesive composition comprises about 90% (by total weight of the composition) of the hot-melt acrylate-based adhesive.

3. The absorbent article as set forth in claim 1 wherein the skin benefit agent is tocopherol.

4. The absorbent article as set forth in claim 1 wherein the adhesive composition comprises about 6% (by total weight of the composition) skin benefit agent.

5. The absorbent article as set forth in claim 1 wherein the matrix is selected from the group consisting of a channel-like matrix and a pore-like matrix, the matrix being capable of allowing controlled-release of the skin benefit agent.

6. The absorbent article as set forth in claim 1 wherein the body-facing surface comprises from about 10 gram per square meter to about 400 grams per square meter skin-adhesive composition.

\* \* \* \* \*